United States Patent [19]
Moineau et al.

[11] Patent Number: 5,824,523
[45] Date of Patent: Oct. 20, 1998

[54] ISOLATED DNA ENCODING ENZYME FOR PHAGE RESISTANCE

[75] Inventors: Sylvain Moineau, Bradenton, Fla.; Shirley A. Walker, Raleigh, N.C.; Ebenezer R. Vedamuthu, Bradenton; Peter A. Vandenbergh, Sarasota, both of Fla.

[73] Assignee: Quest International Flavors & Food Ingredients Company, Division of Indopco, Inc., Bridgewater, N.J.

[21] Appl. No.: 424,641

[22] Filed: Apr. 19, 1995

Related U.S. Application Data

[63] Continuation-in-part of Ser. No. 366,480, Dec. 30, 1994, abandoned.

[51] Int. Cl.⁶ .............. C12N 15/09; C12N 1/21; C12N 15/63; C07H 21/04
[52] U.S. Cl. .................. 435/172.3; 435/252.3; 435/252.33; 435/320.1; 536/23.2
[58] Field of Search .................. 435/172.3, 252.3, 435/252.33, 320.1; 536/23.2

[56] References Cited

U.S. PATENT DOCUMENTS

| | | | |
|---|---|---|---|
| 4,530,904 | 7/1985 | Hershberger et al. | 435/172.3 |
| 4,883,756 | 11/1989 | Klaenhammer et al. | 435/252.3 |
| 4,931,396 | 6/1990 | Klaenhammer et al. | 435/252.3 |
| 5,019,506 | 5/1991 | Daly et al. | 435/172.3 |

FOREIGN PATENT DOCUMENTS

| | | |
|---|---|---|
| 0316677 | 5/1989 | European Pat. Off. . |
| 0452224 | 10/1991 | European Pat. Off. . |

OTHER PUBLICATIONS

Sing, W.D. et al. (1991) "Characterization of restriction-modification plasmids from *lactococcus lactis* ssp. *cremoris* and their effects when combined with pTR2030" J. Dairy Sci. 74(4):1133–1144.

Mercenier, A. et al. (Dec. 1989) "Genetics of *Streptococcus Thermophilus*: a review" J. Dairy Sci. 72(12):3444–3454.

Sing, W.D. (1989) "Mechanisms of pphage resistance encoded by conjugative plasmids of lactococci"Diss. Abst. Int'l. 52(3B):1227.

Sanders, M.E. et al. (Aug. 1990) "Cloning of phage resistance genes from *Lactococcus lactis* ssp. *cremoris* KH" J. Dairy Sci. 73(8):2044–2053.

Mollet, B., et al., Lait 73:175–180 (1993).

Mercenier, A., FEMS Microbiology Reviews 87 61–78 (1990).

Lacks, S.A., et al., Cell, 46:993–1000 (1986).

Klaenhammer, Todd R., Food Biotechnology, pp. 675–681 (Aug. 1991).

Hill, C., FEMS Microbiol. Rev. 12:87–108 (1993).

Sanders, M.E., et al., Appl. Environ. Microbiol. 40:500–506 (1980).

Harrington, A., et al., Appl. Environ. Microbiol. 57:3405–3409 (1991).

Jarvis, A. W., et al., Appl. Environ. Microbiol. 55:1537–1543 (1988).

Sanders, M. E., et al., Appl. Environ. Microbiol. 52:1001–1007 (1986).

Ward, A. C., et al., J. Dairy Sci. 75:683–691 (1992).

Alatossava, T., et al., Appl. Environ. Microbiol. 57:1346–1353 (1991).

(List continued on next page.)

*Primary Examiner*—Robert A. Wax
*Assistant Examiner*—Kawai Lau
*Attorney, Agent, or Firm*—Ian C. McLeod

[57] ABSTRACT

An isolated DNA of a *Lactococcus lactis* showing a SEQ ID NO: 1 encoding a restriction and twp modification enzymes (R/M SEQ ID NO: 2, 3 and 4). The isolated DNA is used to transform sensitive dairy cultures, such as *Lactococcus lactis* and *Streptococcus thermophilus*, to provide phage resistance. *Escherichia coli* can be used to produce endonucleases.

24 Claims, 11 Drawing Sheets

OTHER PUBLICATIONS

Hill, C., et al., J. Bacteriol. 173:4363–4370 (1991).
Moineau, S., et al., Appl. Enviroin. Microbiol. 59:197–202 (1993).
Jarvis, A. W., et al., Intervirology 32:2–9 (1991).
Braun, V., et al., J. Gen. Microbiol. 135:2551–2560 (1989).
Moineau, S., et al., Can. J. Microbiol. 38:875–882 (1992).
Powell, I.A., et al., Can. J. Microbiol. 35:860–866 (1989).
Prevots, F., et al., Appl. Enviroin. Microbiol. 56:2180–2185 (1990).
Moineau, S., et al., J. Dairy Sci. 77:18 suppl. 1 (1992).
Luria, S. E., et al., J. Bacteriol. 64:557–569 (1952).
Bickle, T. A., et al. Microbiol. REv. 57:434–450 (1993).
Dussoix, D., et al., J. Mol. Biol. 5:37–49 (1962).
Wilson, G. G., Nucleic Acids Res. 19:2539–2566 (1991).
Raschke, E., GATA 10:49–60 (1993).
Roberts, R. J., et al., Nucleic Acid Res. 21:3125–3137 (1993).
Wilson, G. G., et al., Annu. Rev. Genet. 25:585–627 (1991).
Klimasauskas, S., et al., Nucleic Acids Res. 17:9823–9832 (1989).
Lauster, R., J. Mol. Biol. 206:313–321 (1989).
McClelland, M., et al., Nucleic Acids Res. 20:2145–2157 (1992).
O'Sullivan D. J., et al., FEMS Microbiol. Rev. 12:P100 (1993).
Fitzgerald, G. F., et al., Nucleic Acid Research 10:8171–8179 (1982).
Davis, R., et al., Appl. Environ. Microbiol. 59:777–785 (1993).
Twomey, D. P., et al., Gene 136:205–209 (1993).
Mayo, B., et al., FEMS Microbiol. Lett. 79:195–198 (1991).
Nyengaard, N., et al., Gene 136:371–372 (1993).
Mercenier et al, Genetic engineering of lactobacilli, leuconostocs and Streptococcus thermopphilus, In M. J. Gasson and W. M. DeVos (ed.), Genetics and biotech.etc. Blackie Acad. Prof.Glaskow,UK pp. 253–293 (1994).
Solaiman, D.K.Y., et al., FEMS Microbiol. Lett. 67:261–266 (1990).
Solaiman, D.K.Y., et al., FEMS Microbiol. Lett. 80:75–80 (1991).
Benbadis, L., et al., Appl. Environ. Microbiol. 57:3677–3678 (1991).
Guimont, C., et al., Appl. Microbiol. Biotechnol. 39:216–220 (1993).
Larbi, et al., J. Dairy REs. 59:349–357 (1992).
McKay, L. L., et al., Appl. Environ. Microbiol. 23:1090–1096 (1972).
J. Josephsen, et al., FEMS Microbiol. Lett. 59:161–166 (1989).
Dao, M. L., et al., Appl. Env. Microb. 49:115–119 (1985).
Terzaghhi, B. E., et al., Appl. Microbiol. 29:807–813 (1975).
Jarvis, A. W., Appl. Environ. Microbiol. 36:785–789 (1978).
Moineau, S., et al., Appl. Envirion. Microbiol. 60:1832–1841 (1994).
O'Sullivan, D.J., et al., Appl. Environ. Microbiol. 59:2730–2733 (1993).
Leblanc, D. J., et al., J. Bacteriol. 140:1112–1115 (1979).
Gonzalez, C. F., et al., Appl. Environ. Microbiol. 46:81–89 (1983).
Holo, H., et al., Appl. Environ. Microbiol. 55:3119–3123 (1989).
Van de Guchte, M., et al., FEMS Microbiol. Rev. 88:73–92 (1992).
Lacks, S. A., et al., In:Genetics and Molecular Biology of Streptococci, Lactococci and Ent.Dunny, G.M., et al (eds) ASM,WASH.D.C.71–76 (1991).
Mannareli, B.M., et al., Proc. Natl. Acad. Sci. 82:4468–4472 (1985).
Ueno, T., et al., Nucleic Acids Res. 10:2309–2313 (1993).
Brooks, J. E., et al., Nucleic Acids Res. 11:837–851 (1983).
Cerritelli, S., et al., Proc. Natl. Acad. Sci. USA 86:9223–9227 (1989).
Chandrasegaran, S., et al., Gene 70:387–392(1988).
de la Campa, A. G., et al., J. Biol. Chem. 263:14696–14702 (1987).
de la Campa, A. G., et al., J. Mol. Biol. 196:457–469 (1987).

1 2 3 4

```
1    CGAGCTTTCTAATGCTTAGTGCTTTAAGATTAGGATAGCACGACTTATTT
51   ATTTTCCAATGAAATTAACTAGCAATTCGGGTATAATATATTTATGAATT
                                                    M  N  L
101  TATTACAAAAAAACAAGATCAACTTACGTCCGTTTACTAAATGGACAGGT
      L  Q  K  N  K  I  N  L  R  P  F  T  K  W  T  G
151  GGGAAAAGGCAACTACTGCCACACATTCAATACCTAATGCCAGAAAAATA
      G  K  R  Q  L  L  P  H  I  Q  Y  L  M  P  E  K  Y
201  CAATCATTTTTTCGAACCTTTTATTGGTGGTGGCGCTTTGTTTTTTGAAC
      N  H  F  F  E  P  F  I  G  G  G  A  L  F  F  E  P
251  CCGCTCCTCAAAAAGCAGTTATTAACGACTTCAATTCTGAGCTTATAAAC
      A  P  Q  K  A  V  I  N  D  F  N  S  E  L  I  N
301  TGTTACCGGCAGATGAAAGATAATCCTGAGCAATTGATAGAATTGTTGAC
      C  Y  R  Q  M  K  D  N  P  E  Q  L  I  E  L  L  T
351  TAATCATCAGCGGGAAAATTCTAAAGAATATTATTTAGACTTACGTTCTT
      N  H  Q  R  E  N  S  K  E  Y  Y  L  D  L  R  S  S
401  CTGATAGAGATGGAAGAATTGATAAGATGAGCGAAGTTGAACGTGCTGCT
      D  R  D  G  R  I  D  K  M  S  E  V  E  R  A  A
451  AGAATTATGTATATGCTACGTGTTGATTTTAATGGTTTATATCGTGTTAA
      R  I  M  Y  M  L  R  V  D  F  N  G  L  Y  R  V  N
501  TTCGAAAAACCAGTTTAATGTGCCTTATGGAAGATATAAAAATCCTAAGA
      S  K  N  Q  F  N  V  P  Y  G  R  Y  K  N  P  K  I
551  TAGTTGATAAAGAATTGATTGAAAGTATTTCCGAGTACTTGAATAACAAT
      V  D  K  E  L  I  E  S  I  S  E  Y  L  N  N  N
601  TCTATTAAGATCATGAGTGGAGATTTTGAAAAAGCCGTTAAAGAAGCACA
      S  I  K  I  M  S  G  D  F  E  K  A  V  K  E  A  Q
651  GGATGGAGATTTTGTTTATTTCGACCCTCCATACATTCCACTTTCTGAAA
      D  G  D  F  V  Y  F  D  P  P  Y  I  P  L  S  E  T
701  CTAGCGCCTTTACTTCTTATACACACGAAGGCTTTAGCTACGAAGATCAA
      S  A  F  T  S  Y  T  H  E  G  F  S  Y  E  D  Q
751  GTTAGGCTAAGAGATTGTTTCAAACAGTTAGATTCAAAAGGGGTATTCGT
      V  R  L  R  D  C  F  K  Q  L  D  S  K  G  V  F  V
801  CATGCTTTCAAATTCTTCAAGCCCTTTAGCGGAGGAATTATATAAAGATT
      M  L  S  N  S  S  S  P  L  A  E  E  L  Y  K  D  F
851  TTAACATCCATAAAATTGAAGCTACTCGAACAAATGGGGCTAAATCATCT
      N  I  H  K  I  E  A  T  R  T  N  G  A  K  S  S
901  AGTCGTGGAAAAATCACTGAAATCATCGTAACCAATTATGGCAATTAACG
      S  R  G  K  I  T  E  I  I  V  T  N  Y  G  N  *
                                                   M  A  I  N  E
```

FIG. 4A

```
 951   AATATAAGTATGGAGGTGTTTTAATGACAAAACCATACTATGAAAAAGAA
             Y  K  Y  G  G  V  L  M  T  K  P  Y  Y  E  K  E

1001   AACGCAATTCTCGTTCACGCAGATTCATTTAAATTATTAGAAAAAATTAA
        N  A  I  L  V  H  A  D  S  F  K  L  L  E  K  I  K

1051   ACCTGAAAGCATGGACATGATATTTGCTGACCCTCCTTACTTTTTAAGTA
         P  E  S  M  D  M  I  F  A  D  P  P  Y  F  L  S  N

1101   ATGGAGGAATGTCAAATTCAGGTGGTCAAATTGTTTCTGTTGATAAAGGG
         G  G  M  S  N  S  G  G  Q  I  V  S  V  D  K  G

1151   GATTGGGATAAAATTTCTTCATTTGAAGAAAAACATGACTTTAATAGACG
        D  W  D  K  I  S  S  F  E  E  K  H  D  F  N  R  R

1201   TTGGATTAGGTTAGCAAGATTGGTTTTAAAACCCAACGGAACTATTTGGG
         W  I  R  L  A  R  L  V  L  K  P  N  G  T  I  W  V

1251   TTTCCGGAAGCCTTCATAACATATATTCTGTCGGGATGGCGCTGGAACAG
         S  G  S  L  H  N  I  Y  S  V  G  M  A  L  E  Q

1301   GAAGGTTTCAAAATCTTAAATAATATAACTTGGCAAAAGACAAATCCTGC
        E  G  F  K  I  L  N  N  I  T  W  Q  K  T  N  P  A

1351   ACCTAATCTATCATGTCGGTACTTCACCCACTCTACAGAGACAATTTTAT
         P  N  L  S  C  R  Y  F  T  H  S  T  E  T  I  L  W

1401   GGGCAAGAAAGAACGATAAAAAATCTCGCCATTATTATAACTATGAATTG
         A  R  K  N  D  K  K  S  R  H  Y  Y  N  Y  E  L

1451   ATGAAAGAGTTTAATGACGGGAAACAAATGAAAGATGTTTGGACAGGTAG
        M  K  E  F  N  D  G  K  Q  M  K  D  V  W  T  G  S

1501   TCTGACAAAAAAATCAGAAAAATGGGCTGGGAAACATCCAACTCAGAAGC
         L  T  K  K  S  E  K  W  A  G  K  H  P  T  Q  K  P

1551   CAGAGTATATTTTAGAACGGATAATCTTAGCTAGTACAAAGGAAAATGAT
         E  Y  I  L  E  R  I  I  L  A  S  T  K  E  N  D

1601   TATATTTTAGACCCTTTCGTCGGAAGTGGAACTACTGGTGTAGTAGCCAA
         Y  I  L  D  P  F  V  G  S  G  T  T  G  V  V  A  K

1651   GAGATTGGGGCGTAAATTTATTGGGATTGATTCTGAGAAGAATATCTTA
         R  L  G  R  K  F  I  G  I  D  S  E  K  E  Y  L  K

1701   AAATTGCTAAAAAAAGGCTAAATAAGGAGCAACATATGGACTTTAATAA
         I  A  K  K  R  L  N  K  G  *
                                       M  D  F  N  N

1751   TTACATCGGTTTAGAATCTGACGATAGATTAAATGCTTTTATGGCAACAC
         Y  I  G  L  E  S  D  D  R  L  N  A  F  M  A  T  L

1801   TTTCCGTAACTAATAGAACTCCCGAATACTACGTGAACTGGGAAAAAGTT
         S  V  T  N  R  T  P  E  Y  Y  V  N  W  E  K  V

1851   GAACGTGAAACACGAAAATTTGAATTAGAACTAAATACTTTAAACTATCT
        E  R  E  T  R  K  F  E  L  E  L  N  T  L  N  Y  L
```

FIG. 4B

```
1901  CATTGGGAAAGAAGATATTTATAGTGAAGCACTTGAACTATTTACCAATC
       I  G  K  E  D  I  Y  S  E  A  L  E  L  F  T  N  Q

1951  AACCTGAATTGCTTAAAGCTATTCCTAGTTTGATTGCTAGTAGAGATACA
        P  E  L  L  K  A  I  P  S  L  I  A  S  R  D  T

2001  TCTTTAGATATACTAAACATTGACGAAAATGATGATATGAGTTTTGAACA
       S  L  D  I  L  N  I  D  E  N  D  D  M  S  F  E  Q

2051  ACTTAACTTTCTTGTTATCGACGAAAATTGTATCGCTGATTATGTAGACT
        L  N  F  L  V  I  D  E  N  C  I  A  D  Y  V  D  F

2101  TTATTAACCAGGCAGGTTTACTAGATTTTCTACAGAATAAAGCAAAACGT
       I  N  Q  A  G  L  L  D  F  L  Q  N  K  A  K  R

2151  TCTCTGGTAGACTATGTGTATGGTGTTGAAGCAGGGCTTGATAGCAATGC
       S  L  V  D  Y  V  Y  G  V  E  A  G  L  D  S  N  A

2201  TCGAAAAAACCGAAGCGGTACAACCATGGAGGGGATTTTAGAACGTACTG
        R  K  N  R  S  G  T  T  M  E  G  I  L  E  R  T  V

2251  TTTCAAAAATAGCTCAAGAGAAAGGGCTTGAATGGAAGCCACAGGCAACC
        S  K  I  A  Q  E  K  G  L  E  W  K  P  Q  A  T

2301  GCTTCTTTTATCAAGTCTCAATGGGACATAGAAGTCCCTGTAGATAAATC
       A  S  F  I  K  S  Q  W  D  I  E  V  P  V  D  K  S

2351  AAAAAGACGCTTTGATGCAGCAGTTTACTCTCGTGCGCTCAATAAGGTTT
        K  R  R  F  D  A  A  V  Y  S  R  A  L  N  K  V  W

2401  GGCTCATAGAAACAAATTACTACGGCGGTGGAGGAAGTAAACTCAAAGCA
        L  I  E  T  N  Y  Y  G  G  G  G  S  K  L  K  A

2451  GTTGCTGGAGAATTTACAGAATTGAGTCAGTTTGTAAAAACATCAAAAGA
       V  A  G  E  F  T  E  L  S  Q  F  V  K  T  S  K  D

2501  TAATGTTGAATTTGTATGGGTAACAGACGGCCAAGGGTGGAAATTTTCCC
        N  V  E  F  V  W  V  T  D  G  Q  G  W  K  F  S  R

2551  GCTTACCACTTGCAGAAGCTTTCGGACACATCGATAACGTTTTCAATCTA
        L  P  L  A  E  A  F  G  H  I  D  N  V  F  N  L

2601  ACCATGTTGAAAGAAGGTTTCTTATCTGATTTATTCGAAAAGAAATTTA
       T  M  L  K  E  G  F  L  S  D  L  F  E  K  E  I  *

2651  AAAAGACAGAGAATCTCTGTCTTTTTAAATTTCAATTCCTTCCTTCTGCT
2701  AGCTATAACTTTCCAAAAAACCTGAAAAACGGTTCTGTTGCAATTGTATG
2751  TGGGGTCGGAACTTACTACTATATCATGAGAAATGAAGATTAAAGTTGAA
2801  ACAAAAAAACAGATTATTTTAAAATGTAAATCTGTTTTTGTTTGGGCTGA
2851  TTTTATCACACCAATTCTATGTTCAGAAAATGGTCATTTTCTGGACACTC
2901  TTCTTTTGTTATTAAAACTCTCAAAATCATTTACATTTATTGTTCATTAA
2951  CCCGTAATTTATTCTATGTTCATTTATAGATATC
```

FIG. 4C

```
                                                                            Motif I
                        *  ** *** **  **         *  *        * *  *          ***       *
M.LlaIIA     MNLLQKNKINLRPFTKWTGGKRQLLPHIQYLMPE--KYNHF--FEPFIGGGALFF-----EPAPQKAVINDFNSELINC    70
M.DpnII      MKIKEIKKVTLQPFTKWTGGKRQLLPVIRELIPKTYNRY----FEPFVGGGALFF-----DLAPKDAVINDFNAELINC    70
M.MboA            MKPPIKWAGGKNSLLDEIQKRLPDFVHSQDFCLVEPFVGGAVSLWALSDLPHLKQLVINDCNADLINV            69
Dam                MKKNRAFLKWAGGKYPLLDDIKRHLP---KGE--CLVEPFVGAGSVFL-----NTDFSRYILADINSDLISL            62

*                          *         *                  *     ***        *
M.LlaIIA     YRQMKDNPEQLIELLTN--HQRENSKEYYLDLRSS-----DRDGRIDKMS-EVERAARIMYLRVDFNGLYRVNSKNQFNV   143
M.DpnII      YQQIKDNPQELIEILKV--HQEYNSKEYYLDLRSA-----DRDERIDMMS-EVQRAARILYMLRVNFNGLYRVNSKNQFNV   143
M.MboA       YQVIKNNPDDLIGYIEN--LQSHYDKLTDLESKKPYFYHKRDVFNQRTSNDIEQAGLFIFLNKSAFNGLYRVNKNNQFNV   147
Dam          YNIVKMRTDEYVQAARELFVPETNCAEVYYQF------REEFNKSQD-PFRRAVLFLYLNRYGYNGLCRYNLRGEFNV    133

Motif II
             *  *  * **                                       * **** *                *
M.LlaIIA     PYGRYKNPKIVDKELIESISEYLNNNSIKIMSGDFEKAVKEAQDG--DFVYFDPPYIPLSETSAPTSYTHEGFSYEDQ   219
M.DpnII      PYGRYKNPKIVDEELISAISVYINNNQLEIKVGDFEKAIVDVRTG--DFVYFDPPYIPLSETSAPTSYTHEGFSFADQ   219
M.MboA       PIGNYKKPTFVDKENILNISKKLQN--TKILSGDFELVLAHLPNNFPCLFYLDPPYRPISDTASFTSYSDNGFDDNEQ   223
Dam          PFGRYKKPYFPEAELYH--FAE--KAQNAFFYCESYADSMARADDA--SVVYCDPPYAPLSATANFTAYHTNSFTLEQQ   206

*                                                       *
M.LlaIIA     VRLRDCFKQLDSKGVFVMLS------NSSSPLAEELYKDFNIHKIEATRTNGAKSSSRGKITEIIVTNYGN           284
M.DpnII      VRLRDAFKRLSDTGAYVMLS------NSSSALVEELYKDFNIHYVEATRTNGAKSSSRGKISEIIVTNYEK           284
M.MboA       KRLANFCKKIDKLGHYFLLSNSDPKNTNSSDEFFDELYQDFKIERIQANRTISANSNGRKKVNEIIVSNGV           294
Dam          AHLAEIAEGLVERHIPVLIS------NHDTMLTREWYQRAKLHVVKVRRSISSNGGTRKKVDELLALYKPGVVSPAKK   278
```

FIG. 5A

```
                                                                    Motif II
                              *                   * * ********    ***
M.LlaIIB    MAINEYKYGGVLMTKPYYEKENA--ILVHADSFKLLEKIKPESMDMIFADPPYFL-SNGGMSNSGGQIVSVDKGDWDK    75
M.DpnA      MKNNEYKYGGVLMTKPYYNKNKM--ILVHSDTFKFLSKMKPESMDMIFADPPYFL-SNGGISNSGGQVVSVDKGDWDK    75
M.MboC                       MRIKPYFESDDKNFNIYQGNCIDFMSHFQDNSIDMIFADPPYFL-SNDGLTFKNSIIQSVNKGEWDK    66
M.HinfI                       MKENINDFL-NTILKG-DCIEKLKTIPNESIDLIPADPPYFPMQTEGKLLRTNGDEFSGVDDEWDK    64

*     *              **   ** *           ***        * ****            *
M.LlaIIB    ISSFEEKHDPNRRWIRLARLVLKPNGTIWVSGSLHNIYSVGMALEQEGFKILNNITWQKTNPAPNLSCRYPTHSTET   152
M.DpnA      ISSFEEKHEPNRKWIRLAKEVLKPNGTVWISGSLHNIYSVGMALEQEGFKILNNITWQKTNPAPNLSCRYPTHSTET   152
M.MboC      NDNEASIYNPNHEWIAQARQLLKDNGTIWISGTHHNIFTVGQVLKENNFKILNIITWEKPNPPPNFSCRYFTYSSEW   143
M.HinfI     FNDFVEYDSPCELWLKECKRILKSTGSIWVIGSFQNIYRIGYIMQNLDFWILNDVIWNKTNPVPNFGGTRFCNAHET   141

*            * **            *            ** ****       *     *         *
M.LlaIIB    ILWARKNDKKSRHYYNYELMKEFNDGKQMKDVWTGSLTKKSEKW---AGK--HPTQKPEYILERIILASTKENDYIL   224
M.DpnA      ILWARKNDKKARHYYNYDLMKELNDGKQMKDVWTGSLTKKVEKW---AGK--HPTQKPEYLLERIILASTKEGDYIL   224
M.MboC      IIWARKH-SKIPHYFNYDLMKKLNGDKQQKDIWRLPAVGSWEKT---QGK--HPTQKPLGLLSRIILSSTQKDDLIL   214
M.HinfI     MLWCSKC-KKNKFTFNYKTMKHLNQEKQERSVWSLSLCTGKERIKDEEGKKAHSTQKPESLLYKVILSSSKPNDVVL   217

Motif I
            *** * ****                                        *
M.LlaIIB    DPFVGSGTTGVVAKRLGRKFIGIDSEKEYLKIAKKRLNKGATYGL                                  269
M.DpnA      DPFVGSGTTGVVAKRLGRRFIGIDAEKEYLKIARKRLEAENETN                                   268
M.MboC      DPFSGSGTTGIAGVLLDRNYIGIEQELEFLELSKRRYHEITPVLKNEFKQKIRKQISAI                    273
M.HinfI     DPFFGTGTTGAVAKALGRNYIGIEREQKYIDVAEKRLREIKPNPNDIELLSLEIKPPKVPMKTLIEADFL         287
```

FIG. 5B

```
R.LlaII                                                                            79
R.DpnII          MDFNNYIGLESDDRLNAFMATLSVTNRTPEYYVNWEKVERETRKFELELNTLNYLIGKEDIYSEALELFTNQPELLKAI   71
R.MboI           MKQTRNFDEWLSTMTDTVADWTYYTDFPKVYKNVSSIKVALNIMNSLIGSKNIQEDFLDLYQNYPEILKVV             69
                 MKLAFDDFLNSMSETNTTLDYFTDFDKVKKNVAQIEIHLNQLNYLLGKDDLKQAVYDLYAECPNAFSIL
                  ***              *          *      *       *****           *

R.LlaII          PSLIASRDTSLDILNIDENDDMSFEQLNFLVIDENCIADYVDFINQAGLLDFLQNKAKRSLVDYVYGVEAGLDSNAR       156
R.DpnII          PLLIAKRLRDTIIVK-DPIKDFYFD----FSKRNYSIEEYTMFLEKSGIFDLLQNHLVSNLVDYVTGVEVGMDTNGR       143
R.MboI           EILIAVRKKE-QKKSLDEKGQVVTLNSYF-----QSADKIIDFLNNTGLADVFRDKNIKNLVDYVFGIEVGLDTNAR       140
                  *** *  *      *   *  *              *      *  *  *    *     *****  * *  *

R.LlaII          KNRSGTTMEGILERTVSKIAQEKGLEWKPQATASFIKSQWDIEVPV----DKSKRRFPDAAVYSRALNKVWLIETNYYG   230
R.DpnII          KNRTGDAMENIVQSYLEAEGYILGENLFKEIEQNEIEEIFSVDLSAITNDGNTVKRPDFVI--KNEQVLYLIEVNFYS   219
R.MboI           KNRGGDNM---SKAVQLLFDNADIYYKEVRNTIFT---DIE-SL----GADVKQPDFVI----KTKRKTYVIETNYYN   204
                 ***    *      *  *      *    *  *       *  *         * * *       *    ** * *

R.LlaII          GGGSKLKAVAGEFTELSQFVKTSKDNVEPVWTDGQGWKFSRLPLAEAFGHIDNVFNLTMLKEGFLSDLFEKEI         304
R.DpnII          GSGSKLNETARSYKMIAEETKAI-PNVEPMWITDGQGWYKAKNNLRETFDILPFLYNINDLEHNILKNLK            288
R.MboI           SGGSKLNEVARAYTDVAPKINQYSQ-YEPVWITDGQGWKTAKNKLQEAYTHIPSVYNLYTL-HGFIEQLNSEGVIKDW   280
                  ****                        ** *****                                *
```

FIG. 5C

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2987 base pairs
        ( B ) TYPE: Nucleic Acid
        ( C ) STRANDEDNESS: Double
        ( D ) TOPOLOGY: Linear ( i i ) MOLECULE TYPE: Peptide ( x i ) SEQUENCE DESCRIPTION: SEQ ID NO:1:

```
TCGCGAGCTT  TCTAATGCTT  AGTGCTTTAA  GATTAGGATA  GCACGACTTA        50
TTTATTTTCC  AATGAAATTA  ACTAGCAATT  CGGGTATAAT  ATATTTATGA       100
ATTTATTACA  AAAAAACAAG  ATCAACTTAC  GTCCGTTTAC  TAAATGGACA       150
GGTGGGAAAA  GGCAACTACT  GCCACACATT  CAATACCTAA  TGCCAGAAAA       200
ATACAATCAT  TTTTTCGAAC  CTTTTATTGG  TGGTGGCGCT  TTGTTTTTTG       250
AACCCGCTCC  TCAAAAAGCA  GTTATTAACG  ACTTCAATTC  TGAGCTTATA       300
AACTGTTACC  GGCAGATGAA  AGATAATCCT  GAGCAATTGA  TAGAATTGTT       350
GACTAATCAT  CAGCGGGAAA  ATTCTAAAGA  ATATTATTTA  GACTTACGTT       400
CTTCTGATAG  AGATGGAAGA  ATTGATAAGA  TGAGCGAAGT  TGAACGTGCT       450
GCTAGAATTA  TGTATATGCT  ACGTGTTGAT  TTTAATGGTT  TATATCGTGT       500
TAATTCGAAA  AACCAGTTTA  ATGTGCCTTA  TGGAAGATAT  AAAAATCCTA       550
AGATAGTTGA  TAAAGAATTG  ATTGAAAGTA  TTTCCGAGTA  CTTGAATAAC       600
AATTCTATTA  AGATCATGAG  TGGAGATTTT  GAAAAAGCCG  TTAAAGAAGC       650
ACAGGATGGA  GATTTTGTTT  ATTTCGACCC  TCCATACATT  CCACTTTCTG       700
AAACTAGCGC  CTTTACTTCT  TATACACACG  AAGGCTTTAG  CTACGAAGAT       750
CAAGTTAGGC  TAAGAGATTG  TTTCAAACAG  TTAGATTCAA  AAGGGGTATT       800
CGTCATGCTT  TCAAATTCTT  CAAGCCCTTT  AGCGGAGGAA  TTATATAAAG       850
ATTTTAACAT  CCATAAAATT  GAAGCTACTC  GAACAAATGG  GGCTAAATCA       900
TCTAGTCGTG  GAAAAATCAC  TGAAATCATC  GTAACCAATT  ATGGCAATTA       950
ACGAATATAA  GTATGGAGGT  GTTTTAATGA  CAAAACCATA  CTATGAAAAA      1000
GAAAACGCAA  TTCTCGTTCA  CGCAGATTCA  TTTAAATTAT  TAGAAAAAAT      1050
TAAACCTGAA  AGCATGGACA  TGATATTTGC  TGACCCTCCT  TACTTTTTAA      1100
GTAATGGAGG  AATGTCAAAT  TCAGGTGGTC  AAATTGTTTC  TGTTGATAAA      1150
GGGGATTGGG  ATAAAATTTC  TTCATTTGAA  GAAAAACATG  ACTTTAATAG      1200
ACGTTGGATT  AGGTTAGCAA  GATTGGTTTT  AAAACCCAAC  GGAACTATTT      1250
```

```
GGGTTTCCGG  AAGCCTTCAT  AACATATATT  CTGTCGGGAT  GGCGCTGGAA      1300

CAGGAAGGTT  TCAAAATCTT  AAATAATATA  ACTTGGCAAA  AGACAAATCC      1350

TGCACCTAAT  CTATCATGTC  GGTACTTCAC  CCACTCTACA  GAGACAATTT      1400

TATGGGCAAG  AAAGAACGAT  AAAAAATCTC  GCCATTATTA  TAACTATGAA      1450

TTGATGAAAG  AGTTTAATGA  CGGGAAACAA  ATGAAGATG   TTTGGACAGG      1500

TAGTCTGACA  AAAAAATCAG  AAAATGGGC   TGGGAAACAT  CCAACTCAGA      1550

AGCCAGAGTA  TATTTTAGAA  CGGATAATCT  TAGCTAGTAC  AAAGGAAAAT      1600

GATTATATTT  TAGACCCTTT  CGTCGGAAGT  GGAACTACTG  GTGTAGTAGC      1650

CAAGAGATTG  GGGCGTAAAT  TTATTGGGAT  TGATTCTGAG  AAAGAATATC      1700

TTAAAATTGC  TAAAAAAGG   CTAAATAAG   GAGCAACATA  TGGACTTTAA      1750

TAATTACATC  GGTTTAGAAT  CTGACGATAG  ATTAAATGCT  TTTATGGCAA      1800

CACTTTCCGT  AACTAATAGA  ACTCCCGAAT  ACTACGTGAA  CTGGGAAAAA      1850

GTTGAACGTG  AAACACGAAA  ATTTGAATTA  GAACTAAATA  CTTTAAACTA      1900

TCTCATTGGG  AAAGAAGATA  TTTATAGTGA  AGCACTTGAA  CTATTTACCA      1950

ATCAACCTGA  ATTGCTTAAA  GCTATTCCTA  GTTTGATTGC  TAGTAGAGAT      2000

ACATCTTTAG  ATATACTAAA  CATTGACGAA  AATGATGATA  TGAGTTTTGA      2050

ACAACTTAAC  TTTCTTGTTA  TCGACGAAAA  TTGTATCGCT  GATTATGTAG      2100

ACTTTATTAA  CCAGGCAGGT  TTACTAGATT  TTCTACAGAA  TAAAGCAAAA      2150

CGTTCTCTGG  TAGACTATGT  GTATGGTGTT  GAAGCAGGGC  TTGATAGCAA      2200

TGCTCGAAAA  AACCGAAGCG  GTACAACCAT  GGAGGGGATT  TTAGAACGTA      2250

CTGTTTCAAA  AATAGCTCAA  GAGAAAGGGC  TTGAATGGAA  GCCACAGGCA      2300

ACCGCTTCTT  TTATCAAGTC  TCAATGGGAC  ATAGAAGTCC  CTGTAGATAA      2350

ATCAAAAAGA  CGCTTTGATG  CAGCAGTTTA  CTCTCGTGCG  CTCAATAAGG      2400

TTTGGCTCAT  AGAAACAAAT  TACTACGGCG  GTGGAGGAAG  TAAACTCAAA      2450

GCAGTTGCTG  GAGAATTTAC  AGAATTGAGT  CAGTTTGTAA  AAACATCAAA      2500

AGATAATGTT  GAATTTGTAT  GGGTAACAGA  CGGCCAAGGG  TGGAAATTTT      2550

CCCGCTTACC  ACTTGCAGAA  GCTTTCGGAC  ACATCGATAA  CGTTTTCAAT      2600

CTAACCATGT  TGAAAGAAGG  TTTCTTATCT  GATTTATTCG  AAAAAGAAAT      2650

TTAAAAAGAC  AGAGAATCTC  TGTCTTTTTA  AATTTCAATT  CCTTCCTTCT      2700

GCTAGCTATA  ACTTTCCAAA  AAACCTGAAA  AACGGTTCTG  TTGCAATTGT      2750

ATGTGGGGTC  GGAACTTACT  ACTATATCAT  GAGAAATGAA  GATTAAAGTT      2800

GAAACAAAAA  AACAGATTAT  TTTAAAATGT  AAATCTGTTT  TTGTTTGGGC      2850

TGATTTTATC  ACACCAATTC  TATGTTCAGA  AAATGGTCAT  TTTCTGGACA      2900

CTCTTCTTTT  GTTATTAAAA  CTCTCAAAAT  CATTTACATT  TATTGTTCAT      2950

TAACCCGTAA  TTTATTCTAT  GTTCATTTAT  AGATATC                     2987
```

( 2 ) INFORMATION FOR SEQ ID NO:2:

( i ) SEQUENCE CHARACTERISTICS:
        ( A ) LENGTH: 284 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:2:

| Met | Asn | Leu | Leu | Gln<br>5 | Lys | Asn | Lys | Ile | Asn<br>10 | Leu | Arg | Pro | Phe | Thr<br>15 |
| Lys | Trp | Thr | Gly | Gly<br>20 | Lys | Arg | Gln | Leu | Leu<br>25 | Pro | His | Ile | Gln | Tyr<br>30 |
| Leu | Met | Pro | Glu | Lys<br>35 | Tyr | Asn | His | Phe | Phe<br>40 | Glu | Pro | Phe | Ile | Gly<br>45 |
| Gly | Gly | Ala | Leu | Phe<br>50 | Phe | Glu | Pro | Ala | Pro<br>55 | Gln | Lys | Ala | Val | Ile<br>60 |
| Asn | Asp | Phe | Asn | Ser<br>65 | Glu | Leu | Ile | Asn | Cys<br>70 | Tyr | Arg | Gln | Met | Lys<br>75 |
| Asp | Asn | Pro | Glu | Gln<br>80 | Leu | Ile | Glu | Leu | Leu<br>85 | Thr | Asn | His | Gln | Arg<br>90 |
| Glu | Asn | Ser | Lys | Glu<br>95 | Tyr | Tyr | Leu | Asp | Leu<br>100 | Arg | Ser | Ser | Asp | Arg<br>105 |
| Asp | Gly | Arg | Ile | Asp<br>110 | Lys | Met | Ser | Glu | Val<br>115 | Glu | Arg | Ala | Ala | Arg<br>120 |
| Ile | Met | Tyr | Met | Leu<br>125 | Arg | Val | Asp | Phe | Asn<br>130 | Gly | Leu | Tyr | Arg | Val<br>135 |
| Asn | Ser | Lys | Asn | Gln<br>140 | Phe | Asn | Val | Pro | Tyr<br>145 | Gly | Arg | Tyr | Lys | Asn<br>150 |
| Pro | Lys | Ile | Val | Asp<br>155 | Lys | Glu | Leu | Ile | Glu<br>160 | Ser | Ile | Ser | Glu | Tyr<br>165 |
| Leu | Asn | Asn | Asn | Ser<br>170 | Ile | Lys | Ile | Met | Ser<br>175 | Gly | Asp | Phe | Glu | Lys<br>180 |
| Ala | Val | Lys | Glu | Ala<br>185 | Gln | Asp | Gly | Asp | Phe<br>190 | Val | Tyr | Phe | Asp | Pro<br>195 |
| Pro | Tyr | Ile | Pro | Leu<br>200 | Ser | Glu | Thr | Ser | Ala<br>205 | Phe | Thr | Ser | Tyr | Thr<br>210 |
| His | Glu | Gly | Phe | Ser<br>215 | Tyr | Glu | Asp | Gln | Val<br>220 | Arg | Leu | Arg | Asp | Cys<br>225 |
| Phe | Lys | Gln | Leu | Asp<br>230 | Ser | Lys | Gly | Val | Phe<br>235 | Val | Met | Leu | Ser | Asn<br>240 |
| Ser | Ser | Ser | Pro | Leu<br>245 | Ala | Glu | Glu | Leu | Tyr<br>250 | Lys | Asp | Phe | Asn | Ile<br>255 |
| His | Lys | Ile | Glu | Ala<br>260 | Thr | Arg | Thr | Asn | Gly<br>265 | Ala | Lys | Ser | Ser | Ser<br>270 |
| Arg | Gly | Lys | Ile | Thr<br>275 | Glu | Ile | Ile | Val | Thr<br>280 | Asn | Tyr | Gly | Asn | |

( 2 ) INFORMATION FOR SEQ ID NO:3:

( i ) SEQUENCE CHARACTERISTICS:
        ( A ) LENGTH: 269 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:3:

| Met | Ala | Ile | Asn | Glu<br>5 | Tyr | Lys | Tyr | Gly | Gly<br>10 | Val | Leu | Met | Thr | Lys<br>15 |
| Pro | Tyr | Tyr | Glu | Lys<br>20 | Glu | Asn | Ala | Ile | Leu<br>25 | Val | His | Ala | Asp | Ser<br>30 |

```
Phe  Lys  Leu  Leu  Glu  Lys  Ile  Lys  Pro  Glu  Ser  Met  Asp  Met  Ile
               35              40                            45

Phe  Ala  Asp  Pro  Pro  Tyr  Phe  Leu  Ser  Asn  Gly  Gly  Met  Ser  Asn
               50              55                            60

Ser  Gly  Gly  Gln  Ile  Val  Ser  Val  Asp  Lys  Gly  Asp  Trp  Asp  Lys
               65              70                            75

Ile  Ser  Ser  Phe  Glu  Glu  Lys  His  Asp  Phe  Asn  Arg  Arg  Trp  Ile
               80              85                            90

Arg  Leu  Ala  Arg  Leu  Val  Leu  Lys  Pro  Asn  Gly  Thr  Ile  Trp  Val
               95              100                           105

Ser  Gly  Ser  Leu  His  Asn  Ile  Tyr  Ser  Val  Gly  Met  Ala  Leu  Glu
               110             115                           120

Gln  Glu  Gly  Phe  Lys  Ile  Leu  Asn  Asn  Ile  Thr  Trp  Gln  Lys  Thr
               125             130                           135

Asn  Pro  Ala  Pro  Asn  Leu  Ser  Cys  Arg  Tyr  Phe  Thr  His  Ser  Thr
               140             145                           150

Glu  Thr  Ile  Leu  Trp  Ala  Arg  Lys  Asn  Asp  Lys  Lys  Ser  Arg  His
               155             160                           165

Tyr  Tyr  Asn  Tyr  Glu  Leu  Met  Lys  Glu  Phe  Asn  Asp  Gly  Lys  Gln
               170             175                           180

Met  Lys  Asp  Val  Trp  Thr  Gly  Ser  Leu  Thr  Lys  Lys  Ser  Glu  Lys
               185             190                           195

Trp  Ala  Gly  Lys  His  Pro  Thr  Gln  Lys  Pro  Glu  Tyr  Ile  Leu  Glu
               200             205                           210

Arg  Ile  Ile  Leu  Ala  Ser  Thr  Lys  Glu  Asn  Asp  Tyr  Ile  Leu  Asp
               215             220                           225

Pro  Phe  Val  Gly  Ser  Gly  Thr  Thr  Gly  Val  Val  Ala  Lys  Arg  Leu
               230             235                           240

Gly  Arg  Lys  Phe  Ile  Gly  Ile  Asp  Ser  Glu  Lys  Glu  Tyr  Leu  Lys
               245             250                           255

Ile  Ala  Lys  Lys  Arg  Leu  Asn  Lys  Gly  Ala  Thr  Tyr  Gly  Leu
               260             265
```

( 2 ) INFORMATION FOR SEQ ID NO:4:

( i ) SEQUENCE CHARACTERISTICS:
        ( A ) LENGTH: 304 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:4:

```
Met  Asp  Phe  Asn  Asn  Tyr  Ile  Gly  Leu  Glu  Ser  Asp  Asp  Arg  Leu
               5               10                            15

Asn  Ala  Phe  Met  Ala  Thr  Leu  Ser  Val  Thr  Asn  Arg  Thr  Pro  Glu
               20              25                            30

Tyr  Tyr  Val  Asn  Trp  Glu  Lys  Val  Glu  Arg  Glu  Thr  Arg  Lys  Phe
               35              40                            45

Glu  Leu  Glu  Leu  Asn  Thr  Leu  Asn  Tyr  Leu  Ile  Gly  Lys  Glu  Asp
               50              55                            60

Ile  Tyr  Ser  Glu  Ala  Leu  Glu  Leu  Phe  Thr  Asn  Gln  Pro  Glu  Leu
               65              70                            75

Leu  Lys  Ala  Ile  Pro  Ser  Leu  Ile  Ala  Ser  Arg  Asp  Thr  Ser  Leu
               80              85                            90
```

| | | | | | | | | | | | | |
|---|---|---|---|---|---|---|---|---|---|---|---|---|
|Asp|Ile|Leu|Asn|Ile<br>95|Asp|Glu|Asn|Asp<br>100|Met|Ser|Phe|Glu<br>105|Gln
|Leu|Asn|Phe|Leu|Val<br>110|Ile|Asp|Glu|Asn<br>115|Cys|Ile|Ala|Asp|Tyr|Val<br>120
|Asp|Phe|Ile|Asn|Gln<br>125|Ala|Gly|Leu|Leu|Asp<br>130|Phe|Leu|Gln|Asn|Lys<br>135
|Ala|Lys|Arg|Ser|Leu<br>140|Val|Asp|Tyr|Val|Tyr<br>145|Gly|Val|Glu|Ala|Gly<br>150
|Leu|Asp|Ser|Asn|Ala<br>155|Arg|Lys|Asn|Arg|Ser<br>160|Gly|Thr|Thr|Met|Glu<br>165
|Gly|Ile|Leu|Glu|Arg<br>170|Thr|Val|Ser|Lys|Ile<br>175|Ala|Gln|Glu|Lys|Gly<br>180
|Leu|Glu|Trp|Lys|Pro<br>185|Gln|Ala|Thr|Ala|Ser<br>190|Phe|Ile|Lys|Ser|Gln<br>195
|Trp|Asp|Ile|Glu|Val<br>200|Pro|Val|Asp|Lys|Ser<br>205|Lys|Arg|Arg|Phe|Asp<br>210
|Ala|Ala|Val|Tyr|Ser<br>215|Arg|Ala|Leu|Asn|Lys<br>220|Val|Trp|Leu|Ile|Glu<br>225
|Thr|Asn|Tyr|Tyr|Gly<br>230|Gly|Gly|Gly|Ser|Lys<br>235|Leu|Lys|Ala|Val|Ala<br>240
|Gly|Glu|Phe|Thr|Glu<br>245|Leu|Ser|Gln|Phe|Val<br>250|Lys|Thr|Ser|Lys|Asp<br>255
|Asn|Val|Glu|Phe|Val<br>260|Trp|Val|Thr|Asp|Gly<br>265|Gln|Gly|Trp|Lys|Phe<br>270
|Ser|Arg|Leu|Pro|Leu<br>275|Ala|Glu|Ala|Phe|Gly<br>280|His|Ile|Asp|Asn|Val<br>285
|Phe|Asn|Leu|Thr|Met<br>290|Leu|Lys|Glu|Gly|Phe<br>295|Leu|Ser|Asp|Leu|Phe<br>300
|Glu|Lys|Glu|Ile|

(2) INFORMATION FOR SEQ ID NO:5:

(i) SEQUENCE CHARACTERISTICS:
        (A) LENGTH: 284 Amino Acids
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO:5:

| | | | | | | | | | | | | | | |
|---|---|---|---|---|---|---|---|---|---|---|---|---|---|---|
|Met|Lys|Ile|Lys|Glu<br>5|Ile|Lys|Lys|Val|Thr<br>10|Leu|Gln|Pro|Phe|Thr<br>15
|Lys|Trp|Thr|Gly|Gly<br>20|Lys|Arg|Gln|Leu|Leu<br>25|Pro|Val|Ile|Arg|Glu<br>30
|Leu|Ile|Pro|Lys|Thr<br>35|Tyr|Asn|Arg|Tyr|Phe<br>40|Glu|Pro|Phe|Val|Gly<br>45
|Gly|Gly|Ala|Leu|Phe<br>50|Phe|Asp|Leu|Ala|Pro<br>55|Lys|Asp|Ala|Val|Ile<br>60
|Asn|Asp|Phe|Asn|Ala<br>65|Glu|Leu|Ile|Asn|Cys<br>70|Tyr|Gln|Gln|Ile|Lys<br>75
|Asp|Asn|Pro|Gln|Glu<br>80|Leu|Ile|Glu|Ile|Leu<br>85|Lys|Val|His|Gln|Glu<br>90
|Tyr|Asn|Ser|Lys|Glu<br>95|Tyr|Tyr|Leu|Asp|Leu<br>100|Arg|Ser|Ala|Asp|Arg<br>105
|Asp|Glu|Arg|Ile|Asp<br>110|Met|Met|Ser|Glu|Val<br>115|Gln|Arg|Ala|Ala|Arg<br>120

Ile Leu Tyr Met Leu Arg Val Asn Phe Asn Gly Leu Tyr Arg Val
            125                     130                     135

Asn Ser Lys Asn Gln Phe Asn Val Pro Tyr Gly Arg Tyr Lys Asn
            140                     145                     150

Pro Lys Ile Val Asp Glu Glu Leu Ile Ser Ala Ile Ser Val Tyr
            155                     160                     165

Ile Asn Asn Asn Gln Leu Glu Ile Lys Val Gly Asp Phe Glu Lys
            170                     175                     180

Ala Ile Val Asp Val Arg Thr Gly Asp Phe Val Tyr Phe Asp Pro
            185                     190                     195

Pro Tyr Ile Pro Leu Ser Glu Thr Ser Ala Phe Thr Ser Tyr Thr
            200                     205                     210

His Glu Gly Phe Ser Phe Ala Asp Gln Val Arg Leu Arg Asp Ala
            215                     220                     225

Phe Lys Arg Leu Ser Asp Thr Gly Ala Tyr Val Met Leu Ser Asn
            230                     235                     240

Ser Ser Ser Ala Leu Val Glu Glu Leu Tyr Lys Asp Phe Asn Ile
            245                     250                     255

His Tyr Val Glu Ala Thr Arg Thr Asn Gly Ala Lys Ser Ser Ser
            260                     265                     270

Arg Gly Lys Ile Ser Glu Ile Ile Val Thr Asn Tyr Glu Lys
            275                     280

( 2 ) INFORMATION FOR SEQ ID NO:6:

( i ) SEQUENCE CHARACTERISTICS:
        ( A ) LENGTH: 294 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:6:

Met Lys Pro Phe Ile Lys Trp Ala Gly Gly Lys Asn Ser Leu Leu
              5                      10                      15

Asp Glu Ile Gln Lys Arg Leu Pro Asp Phe Val His Ser Gln Asp
             20                      25                      30

Phe Cys Leu Val Glu Pro Phe Val Gly Gly Ala Val Ser Leu
             35                      40                      45

Trp Ala Leu Ser Asp Leu Pro His Leu Lys Gln Leu Val Ile Asn
             50                      55                      60

Asp Cys Asn Ala Asp Leu Ile Asn Val Tyr Gln Val Ile Lys Asn
             65                      70                      75

Asn Pro Asp Asp Leu Ile Gly Tyr Ile Glu Asn Leu Gln Ser His
             80                      85                      90

Tyr Asp Lys Leu Thr Asp Leu Glu Ser Lys Lys Pro Tyr Phe Tyr
             95                     100                     105

His Lys Arg Asp Val Phe Asn Gln Arg Thr Ser Asn Asp Ile Glu
            110                     115                     120

Gln Ala Gly Leu Phe Ile Phe Leu Asn Lys Ser Ala Phe Asn Gly
            125                     130                     135

Leu Tyr Arg Val Asn Lys Asn Asn Gln Phe Asn Val Pro Ile Gly
            140                     145                     150

Asn Tyr Lys Lys Pro Thr Phe Val Asp Lys Glu Asn Ile Leu Asn
            155                     160                     165

```
Ile  Ser  Lys  Lys  Leu  Gln  Asn  Thr  Lys  Ile  Leu  Ser  Gly  Asp  Phe
               170                 175                          180

Glu  Leu  Val  Leu  Ala  His  Leu  Pro  Asn  Phe  Pro  Cys  Leu  Phe
               185                 190                          195

Tyr  Leu  Asp  Pro  Pro  Tyr  Arg  Pro  Ile  Ser  Asp  Thr  Ala  Ser  Phe
               200                 205                          210

Thr  Ser  Tyr  Ser  Asp  Asn  Gly  Phe  Asp  Asp  Asn  Glu  Gln  Lys  Arg
               215                 220                          225

Leu  Ala  Asn  Phe  Cys  Lys  Lys  Ile  Asp  Lys  Leu  Gly  His  Tyr  Phe
               230                 235                          240

Leu  Leu  Ser  Asn  Ser  Asp  Pro  Lys  Asn  Thr  Asn  Ser  Ser  Asp  Glu
               245                 250                          255

Phe  Phe  Asp  Glu  Leu  Tyr  Gln  Asp  Phe  Lys  Ile  Glu  Arg  Ile  Gln
               260                 265                          270

Ala  Asn  Arg  Thr  Ile  Ser  Ala  Asn  Ser  Asn  Gly  Arg  Lys  Lys  Val
               275                 280                          285

Asn  Glu  Ile  Ile  Val  Ser  Asn  Gly  Val
               290
```

( 2 ) INFORMATION FOR SEQ ID NO:7:

( i ) SEQUENCE CHARACTERISTICS:
        ( A ) LENGTH: 278 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:7:

```
Met  Lys  Lys  Asn  Arg  Ala  Phe  Leu  Lys  Trp  Ala  Gly  Gly  Lys  Tyr
                5                  10                           15

Pro  Leu  Leu  Asp  Asp  Ile  Lys  Arg  His  Leu  Pro  Lys  Gly  Glu  Cys
               20                  25                           30

Leu  Val  Glu  Pro  Phe  Val  Gly  Ala  Gly  Ser  Val  Phe  Leu  Asn  Thr
               35                  40                           45

Asp  Phe  Ser  Arg  Tyr  Ile  Leu  Ala  Asp  Ile  Asn  Ser  Asp  Leu  Ile
               50                  55                           60

Ser  Leu  Tyr  Asn  Ile  Val  Lys  Met  Arg  Thr  Asp  Glu  Tyr  Val  Gln
               65                  70                           75

Ala  Ala  Arg  Glu  Leu  Phe  Val  Pro  Glu  Thr  Asn  Cys  Ala  Glu  Val
               80                  85                           90

Tyr  Tyr  Gln  Phe  Arg  Glu  Glu  Phe  Asn  Lys  Ser  Gln  Asp  Pro  Phe
               95                  100                          105

Arg  Arg  Ala  Val  Leu  Phe  Leu  Tyr  Leu  Asn  Arg  Tyr  Gly  Tyr  Asn
               110                 115                          120

Gly  Leu  Cys  Arg  Tyr  Asn  Leu  Arg  Gly  Glu  Phe  Asn  Val  Pro  Phe
               125                 130                          135

Gly  Arg  Tyr  Lys  Lys  Pro  Tyr  Phe  Pro  Glu  Ala  Glu  Leu  Tyr  His
               140                 145                          150

Phe  Ala  Glu  Lys  Ala  Gln  Asn  Ala  Phe  Phe  Tyr  Cys  Glu  Ser  Tyr
               155                 160                          165

Ala  Asp  Ser  Met  Ala  Arg  Ala  Asp  Asp  Ala  Ser  Val  Val  Tyr  Cys
               170                 175                          180

Asp  Pro  Pro  Tyr  Ala  Pro  Leu  Ser  Ala  Thr  Ala  Asn  Phe  Thr  Ala
               185                 190                          195
```

| Tyr | His | Thr | Asn | Ser     | Phe | Thr | Leu | Glu | Gln     | Gln | Ala | His | Leu | Ala     |
|-----|-----|-----|-----|---------|-----|-----|-----|-----|---------|-----|-----|-----|-----|---------|
|     |     |     |     | 200     |     |     |     |     | 205     |     |     |     |     | 210     |
| Glu | Ile | Ala | Glu | Gly 215 | Leu | Val | Glu | Arg | His 220 | Ile | Pro | Val | Leu | Ile 225 |
| Ser | Asn | His | Asp | Thr 230 | Met | Leu | Thr | Arg | Glu 235 | Trp | Tyr | Gln | Arg | Ala 240 |
| Lys | Leu | His | Val | Val 245 | Lys | Val | Arg | Arg | Ser 250 | Ile | Ser | Ser | Asn | Gly 255 |
| Gly | Thr | Arg | Lys | Lys 260 | Val | Asp | Glu | Leu | Leu 265 | Ala | Leu | Tyr | Lys | Pro 270 |
| Gly | Val | Val | Ser | Pro 275 | Ala | Lys | Lys |     |         |     |     |     |     |         |

( 2 ) INFORMATION FOR SEQ ID NO:8:

( i ) SEQUENCE CHARACTERISTICS:
        ( A ) LENGTH: 268 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:8:

| Met | Lys | Asn | Asn | Glu 5   | Tyr | Lys | Tyr | Gly | Gly 10  | Val | Leu | Met | Thr | Lys 15  |
|-----|-----|-----|-----|---------|-----|-----|-----|-----|---------|-----|-----|-----|-----|---------|
| Pro | Tyr | Tyr | Asn | Lys 20  | Asn | Lys | Met | Ile | Leu 25  | Val | His | Ser | Asp | Thr 30  |
| Phe | Lys | Phe | Leu | Ser 35  | Lys | Met | Lys | Pro | Glu 40  | Ser | Met | Asp | Met | Ile 45  |
| Phe | Ala | Asp | Pro | Pro 50  | Tyr | Phe | Leu | Ser | Asn 55  | Gly | Gly | Ile | Ser | Asn 60  |
| Ser | Gly | Gly | Gln | Val 65  | Val | Ser | Val | Asp | Lys 70  | Gly | Asp | Trp | Asp | Lys 75  |
| Ile | Ser | Ser | Phe | Glu 80  | Glu | Lys | His | Glu | Phe 85  | Asn | Arg | Lys | Trp | Ile 90  |
| Arg | Leu | Ala | Lys | Glu 95  | Val | Leu | Lys | Pro | Asn 100 | Gly | Thr | Val | Trp | Ile 105 |
| Ser | Gly | Ser | Leu | His 110 | Asn | Ile | Tyr | Ser | Val 115 | Gly | Met | Ala | Leu | Glu 120 |
| Gln | Glu | Gly | Phe | Lys 125 | Ile | Leu | Asn | Asn | Ile 130 | Thr | Trp | Gln | Lys | Thr 135 |
| Asn | Pro | Ala | Pro | Asn 140 | Leu | Ser | Cys | Arg | Tyr 145 | Phe | Thr | His | Ser | Thr 150 |
| Glu | Thr | Ile | Leu | Trp 155 | Ala | Arg | Lys | Asn | Asp 160 | Lys | Lys | Ala | Arg | His 165 |
| Tyr | Tyr | Asn | Tyr | Asp 170 | Leu | Met | Lys | Glu | Leu 175 | Asn | Asp | Gly | Lys | Gln 180 |
| Met | Lys | Asp | Val | Trp 185 | Thr | Gly | Ser | Leu | Thr 190 | Lys | Lys | Val | Glu | Lys 195 |
| Trp | Ala | Gly | Lys | His 200 | Pro | Thr | Gln | Lys | Pro 205 | Glu | Tyr | Leu | Leu | Glu 210 |
| Arg | Ile | Ile | Leu | Ala 215 | Ser | Thr | Lys | Glu | Gly 220 | Asp | Tyr | Ile | Leu | Asp 225 |
| Pro | Phe | Val | Gly | Ser 230 | Gly | Thr | Thr | Gly | Val 235 | Val | Ala | Lys | Arg | Leu 240 |

| | | | | | | | | | | | | | | |
|---|---|---|---|---|---|---|---|---|---|---|---|---|---|---|
| Gly | Arg | Arg | Phe | Ile<br>245 | Gly | Ile | Asp | Ala | Glu<br>250 | Lys | Glu | Tyr | Leu | Lys<br>255 |
| Ile | Ala | Arg | Lys | Arg<br>260 | Leu | Glu | Ala | Glu | Asn<br>265 | Glu | Thr | Asn | | |

(2) INFORMATION FOR SEQ ID NO:9:

(i) SEQUENCE CHARACTERISTICS:
        (A) LENGTH: 273 Amino Acids
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO:9:

| | | | | | | | | | | | | | | |
|---|---|---|---|---|---|---|---|---|---|---|---|---|---|---|
| Met | Arg | Ile | Lys | Pro<br>5 | Tyr | Phe | Glu | Ser | Asp<br>10 | Asp | Lys | Asn | Phe | Asn<br>15 |
| Ile | Tyr | Gln | Gly | Asn<br>20 | Cys | Ile | Asp | Phe | Met<br>25 | Ser | His | Phe | Gln | Asp<br>30 |
| Asn | Ser | Ile | Asp | Met<br>35 | Ile | Phe | Ala | Asp | Pro<br>40 | Pro | Tyr | Phe | Leu | Ser<br>45 |
| Asn | Asp | Gly | Leu | Thr<br>50 | Phe | Lys | Asn | Ser | Ile<br>55 | Ile | Gln | Ser | Val | Asn<br>60 |
| Lys | Gly | Glu | Trp | Asp<br>65 | Lys | Asn | Asp | Asn | Glu<br>70 | Ala | Ser | Ile | Tyr | Asn<br>75 |
| Phe | Asn | His | Glu | Trp<br>80 | Ile | Ala | Gln | Ala | Arg<br>85 | Gln | Leu | Leu | Lys | Asp<br>90 |
| Asn | Gly | Thr | Ile | Trp<br>95 | Ile | Ser | Gly | Thr | His<br>100 | His | Asn | Ile | Phe | Thr<br>105 |
| Val | Gly | Gln | Val | Leu<br>110 | Lys | Glu | Asn | Asn | Phe<br>115 | Lys | Ile | Leu | Asn | Ile<br>120 |
| Ile | Thr | Trp | Glu | Lys<br>125 | Pro | Asn | Pro | Pro | Asn<br>130 | Phe | Ser | Cys | Arg<br>135 | |
| Tyr | Phe | Thr | Tyr | Ser<br>140 | Ser | Glu | Trp | Ile | Ile<br>145 | Trp | Ala | Arg | Lys | His<br>150 |
| Ser | Lys | Ile | Pro | His<br>155 | Tyr | Phe | Asn | Tyr | Asp<br>160 | Leu | Met | Lys | Lys | Leu<br>165 |
| Asn | Gly | Asp | Lys | Gln<br>170 | Gln | Lys | Asp | Ile | Trp<br>175 | Arg | Leu | Pro | Ala | Val<br>180 |
| Gly | Ser | Trp | Glu | Lys<br>185 | Thr | Gln | Gly | Lys | His<br>190 | Pro | Thr | Gln | Lys | Pro<br>195 |
| Leu | Gly | Leu | Leu | Ser<br>200 | Arg | Ile | Ile | Leu | Ser<br>205 | Ser | Thr | Gln | Lys | Asp<br>210 |
| Asp | Leu | Ile | Leu | Asp<br>215 | Pro | Phe | Ser | Gly | Ser<br>220 | Gly | Thr | Thr | Gly | Ile<br>225 |
| Ala | Gly | Val | Leu | Leu<br>230 | Asp | Arg | Asn | Tyr | Ile<br>235 | Gly | Ile | Glu | Gln | Glu<br>240 |
| Leu | Glu | Phe | Leu | Glu<br>245 | Leu | Ser | Lys | Arg | Arg<br>250 | Tyr | His | Glu | Ile | Thr<br>255 |
| Pro | Val | Leu | Lys | Asn<br>260 | Glu | Phe | Lys | Gln | Lys<br>265 | Ile | Arg | Lys | Gln | Ile<br>270 |
| Ser | Ala | Ile | | | | | | | | | | | | |

(2) INFORMATION FOR SEQ ID NO:10:

(i) SEQUENCE CHARACTERISTICS:
        (A) LENGTH: 287 Amino Acids ( B ) TYPE: Amino Acid
( C ) STRANDEDNESS: Single
( D ) TOPOLOGY: Linear ( i i ) MOLECULE TYPE: Peptide ( x i ) SEQUENCE DESCRIPTION: SEQ ID NO:10:

| Met | Met | Lys | Glu | Asn<br>5 | Ile | Asn | Asp | Phe | Leu<br>10 | Asn | Thr | Ile | Leu | Lys<br>15 |
|---|---|---|---|---|---|---|---|---|---|---|---|---|---|---|
| Gly | Asp | Cys | Ile | Glu<br>20 | Lys | Leu | Lys | Thr | Ile<br>25 | Pro | Asn | Glu | Ser | Ile<br>30 |
| Asp | Leu | Ile | Phe | Ala<br>35 | Asp | Pro | Pro | Tyr | Phe<br>40 | Met | Gln | Thr | Glu | Gly<br>45 |
| Lys | Leu | Leu | Arg | Thr<br>50 | Asn | Gly | Asp | Glu | Phe<br>55 | Ser | Gly | Val | Asp | Asp<br>60 |
| Glu | Trp | Asp | Lys | Phe<br>65 | Asn | Asp | Phe | Val | Glu<br>70 | Tyr | Asp | Ser | Phe | Cys<br>75 |
| Glu | Leu | Trp | Leu | Lys<br>80 | Glu | Cys | Lys | Arg | Ile<br>85 | Leu | Lys | Ser | Thr | Gly<br>90 |
| Ser | Ile | Trp | Val | Ile<br>95 | Gly | Ser | Phe | Gln | Asn<br>100 | Ile | Tyr | Arg | Ile | Gly<br>105 |
| Tyr | Ile | Met | Gln | Asn<br>110 | Leu | Asp | Phe | Trp | Ile<br>115 | Leu | Asn | Asp | Val | Ile<br>120 |
| Trp | Asn | Lys | Thr | Asn<br>125 | Pro | Val | Pro | Asn | Phe<br>130 | Gly | Gly | Thr | Arg | Phe<br>135 |
| Cys | Asn | Ala | His | Glu<br>140 | Thr | Met | Leu | Trp | Cys<br>145 | Ser | Lys | Cys | Lys | Lys<br>150 |
| Asn | Lys | Phe | Thr | Phe<br>155 | Asn | Tyr | Lys | Thr | Met<br>160 | Lys | His | Leu | Asn | Gln<br>165 |
| Glu | Lys | Gln | Glu | Arg<br>170 | Ser | Val | Trp | Ser | Leu<br>175 | Ser | Leu | Cys | Thr | Gly<br>180 |
| Lys | Glu | Arg | Ile | Lys<br>185 | Asp | Glu | Glu | Gly | Lys<br>190 | Lys | Ala | His | Ser | Thr<br>195 |
| Gln | Lys | Pro | Glu | Ser<br>200 | Leu | Leu | Tyr | Lys | Val<br>205 | Ile | Leu | Ser | Ser | Ser<br>210 |
| Lys | Pro | Asn | Asp | Val<br>215 | Val | Leu | Asp | Pro | Phe<br>220 | Phe | Gly | Thr | Gly | Thr<br>225 |
| Thr | Gly | Ala | Val | Ala<br>230 | Lys | Ala | Leu | Gly | Arg<br>235 | Asn | Tyr | Ile | Gly | Ile<br>240 |
| Glu | Arg | Glu | Gln | Lys<br>245 | Tyr | Ile | Asp | Val | Ala<br>250 | Glu | Lys | Arg | Leu | Arg<br>255 |
| Glu | Ile | Lys | Pro | Asn<br>260 | Pro | Asn | Asp | Ile | Glu<br>265 | Leu | Leu | Ser | Leu | Glu<br>270 |
| Ile | Lys | Pro | Pro | Lys<br>275 | Val | Pro | Met | Lys | Thr<br>280 | Leu | Ile | Glu | Ala | Asp<br>285 |
| Phe | Leu | | | | | | | | | | | | | |

( 2 ) INFORMATION FOR SEQ ID NO:11:

( i ) SEQUENCE CHARACTERISTICS:
( A ) LENGTH: 288 Amino Acids
( B ) TYPE: Amino Acid
( C ) STRANDEDNESS: Single
( D ) TOPOLOGY: Linear ( i i ) MOLECULE TYPE: Peptide ( x i ) SEQUENCE DESCRIPTION: SEQ ID NO:11:

-continued

| | | | | | | | | | | | | | | |
|---|---|---|---|---|---|---|---|---|---|---|---|---|---|---|
| Met | Lys | Gln | Thr | Arg | Asn | Phe | Asp | Glu | Trp | Leu | Ser | Thr | Met | Thr |
| | | | | 5 | | | | 10 | | | | | | 15 |
| Asp | Thr | Val | Ala | Asp | Trp | Thr | Tyr | Tyr | Thr | Asp | Phe | Pro | Lys | Val |
| | | | | 20 | | | | 25 | | | | | | 30 |
| Tyr | Lys | Asn | Val | Ser | Ser | Ile | Lys | Val | Ala | Leu | Asn | Ile | Met | Asn |
| | | | | 35 | | | | 40 | | | | | | 45 |
| Ser | Leu | Ile | Gly | Ser | Lys | Asn | Ile | Gln | Glu | Asp | Phe | Leu | Asp | Leu |
| | | | | 50 | | | | 55 | | | | | | 60 |
| Tyr | Gln | Asn | Tyr | Pro | Glu | Ile | Leu | Lys | Val | Val | Pro | Leu | Leu | Ile |
| | | | | 65 | | | | 70 | | | | | | 75 |
| Ala | Lys | Arg | Leu | Arg | Asp | Thr | Ile | Ile | Val | Lys | Asp | Pro | Ile | Lys |
| | | | | 80 | | | | 85 | | | | | | 90 |
| Asp | Phe | Tyr | Phe | Asp | Phe | Ser | Lys | Arg | Asn | Tyr | Ser | Ile | Glu | Glu |
| | | | | 95 | | | | 100 | | | | | | 105 |
| Tyr | Thr | Met | Phe | Leu | Glu | Lys | Ser | Gly | Ile | Phe | Asp | Leu | Leu | Gln |
| | | | | 110 | | | | 115 | | | | | | 120 |
| Asn | His | Leu | Val | Ser | Asn | Leu | Val | Asp | Tyr | Val | Thr | Gly | Val | Glu |
| | | | | 125 | | | | 130 | | | | | | 135 |
| Val | Gly | Met | Asp | Thr | Asn | Gly | Arg | Lys | Asn | Arg | Thr | Gly | Asp | Ala |
| | | | | 140 | | | | 145 | | | | | | 150 |
| Met | Glu | Asn | Ile | Val | Gln | Ser | Tyr | Leu | Glu | Ala | Glu | Gly | Tyr | Ile |
| | | | | 155 | | | | 160 | | | | | | 165 |
| Leu | Gly | Glu | Asn | Leu | Phe | Lys | Glu | Ile | Glu | Gln | Asn | Glu | Ile | Glu |
| | | | | 170 | | | | 175 | | | | | | 180 |
| Glu | Ile | Phe | Ser | Val | Asp | Leu | Ser | Ala | Ile | Thr | Asn | Asp | Gly | Asn |
| | | | | 185 | | | | 190 | | | | | | 195 |
| Thr | Val | Lys | Arg | Phe | Asp | Phe | Val | Ile | Lys | Asn | Glu | Gln | Val | Leu |
| | | | | 200 | | | | 205 | | | | | | 210 |
| Tyr | Leu | Ile | Glu | Val | Asn | Phe | Tyr | Ser | Gly | Ser | Gly | Ser | Lys | Leu |
| | | | | 215 | | | | 220 | | | | | | 225 |
| Asn | Glu | Thr | Ala | Arg | Ser | Tyr | Lys | Met | Ile | Ala | Glu | Glu | Thr | Lys |
| | | | | 230 | | | | 235 | | | | | | 240 |
| Ala | Ile | Pro | Asn | Val | Glu | Phe | Met | Trp | Ile | Thr | Asp | Gly | Gln | Gly |
| | | | | 245 | | | | 250 | | | | | | 255 |
| Trp | Tyr | Lys | Ala | Lys | Asn | Asn | Leu | Arg | Glu | Thr | Phe | Asp | Ile | Leu |
| | | | | 260 | | | | 265 | | | | | | 270 |
| Pro | Phe | Leu | Tyr | Asn | Ile | Asn | Asp | Leu | Glu | His | Asn | Ile | Leu | Lys |
| | | | | 275 | | | | 280 | | | | | | 285 |
| Asn | Leu | Lys | | | | | | | | | | | | |

( 2 ) INFORMATION FOR SEQ ID NO:12:

( i ) SEQUENCE CHARACTERISTICS:
        ( A ) LENGTH: 280 Amino Acids
        ( B ) TYPE: Amino Acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:12:

| | | | | | | | | | | | | | | |
|---|---|---|---|---|---|---|---|---|---|---|---|---|---|---|
| Met | Lys | Leu | Ala | Phe | Asp | Asp | Phe | Leu | Asn | Ser | Met | Ser | Glu | Thr |
| | | | | 5 | | | | 10 | | | | | | 15 |
| Asn | Thr | Thr | Leu | Asp | Tyr | Phe | Thr | Asp | Phe | Asp | Lys | Val | Lys | Lys |
| | | | | 20 | | | | 25 | | | | | | 30 |
| Asn | Val | Ala | Gln | Ile | Glu | Ile | His | Leu | Asn | Gln | Leu | Asn | Tyr | Leu |
| | | | | 35 | | | | 40 | | | | | | 45 |

| | | | | | | | | | | | | |
|---|---|---|---|---|---|---|---|---|---|---|---|---|
| Leu | Gly | Lys | Asp | Asp 50 | Leu | Lys | Gln | Ala | Val 55 | Tyr | Asp | Leu | Tyr | Ala 60 |
| Glu | Cys | Pro | Asn | Ala 65 | Phe | Ser | Ile | Leu | Glu 70 | Ile | Leu | Ile | Ala | Val 75 |
| Arg | Lys | Lys | Glu | Gln 80 | Lys | Lys | Ser | Leu | Asp 85 | Glu | Lys | Gly | Gln | Val 90 |
| Val | Thr | Leu | Asn | Ser 95 | Tyr | Phe | Gln | Ser | Ala 100 | Asp | Lys | Ile | Ile | Asp 105 |
| Phe | Leu | Asn | Asn | Thr 110 | Gly | Leu | Ala | Asp | Val 115 | Phe | Arg | Asp | Lys | Asn 120 |
| Ile | Lys | Asn | Leu | Val 125 | Asp | Tyr | Val | Phe | Gly 130 | Ile | Glu | Val | Gly | Leu 135 |
| Asp | Thr | Asn | Ala | Arg 140 | Lys | Asn | Arg | Gly | Gly 145 | Asp | Asn | Met | Ser | Lys 150 |
| Ala | Val | Gln | Leu | Leu 155 | Phe | Asp | Asn | Ala | Asp 160 | Ile | Tyr | Tyr | Lys | Lys 165 |
| Glu | Val | Arg | Asn | Thr 170 | Ile | Phe | Thr | Asp | Ile 175 | Glu | Ser | Leu | Gly | Ala 180 |
| Asp | Val | Lys | Gln | Phe 185 | Asp | Phe | Val | Ile | Lys 190 | Thr | Lys | Arg | Lys | Thr 195 |
| Tyr | Val | Ile | Glu | Thr 200 | Asn | Tyr | Tyr | Asn | Ser 205 | Gly | Gly | Ser | Lys | Leu 210 |
| Asn | Glu | Val | Ala | Arg 215 | Ala | Tyr | Thr | Asp | Val 220 | Ala | Pro | Lys | Ile | Asn 225 |
| Gln | Tyr | Ser | Gln | Tyr 230 | Glu | Phe | Val | Trp | Ile 235 | Thr | Asp | Gly | Gln | Gly 240 |
| Trp | Lys | Thr | Ala | Lys 245 | Asn | Lys | Leu | Gln | Glu 250 | Ala | Tyr | Thr | His | Ile 255 |
| Pro | Ser | Val | Tyr | Asn 260 | Leu | Tyr | Thr | Leu | His 265 | Gly | Phe | Ile | Glu | Gln 270 |
| Leu | Asn | Ser | Glu | Gly 275 | Val | Ile | Lys | Asp | Trp 280 | | | | | |

ISOLATED DNA ENCODING ENZYME FOR PHAGE RESISTANCE

CROSS-REFERENCE TO RELATED APPLICATION

This application is a continuation-in-part of application Ser. No 08/366,480, filed Dec. 30, 1994, now abandoned.

BACKGROUND OF THE INVENTION (1) Field of the Invention

The present invention relates to transformed dairy cultures with a natural 7.8-kb plasmid pSRQ700 which was isolated from *Lactococcus lactis* subsp. *cremoris* DCH-4, a known strain. pSRQ700 encodes a restriction/modification system named LlaII. When introduced into a phage-sensitive dairy culture, such as *L. lactis,* pSRQ700 confers strong phage resistance against the three most common lactococcal phage species: 936, c2 and P335 found in dairy product fermentations. The LlaII endonuclease was purified and found to cleave the palindromic sequence 5'/GATC-3'. The low copy plasmid pSRQ700 was mapped and the genetic organization of LlaII localized. Cloning and sequencing of the entire LlaII system allowed the identification of three open reading frames. The three genes (LlaIIA, LlaIIB, and LlaIIC) overlapped and are under one promoter. A terminator was found at the end of LlaIIC. The genes LlaIIA and LlaIIB coded for $m^6$A-methyltransferases and LlaIIC for an endonuclease. The native LlaII R/M system from *Lactococcus lactis* is also expressed by and conferred strong phage resistance to various industrial *S. thermophilus* strains. Resistance was observed against phages isolated from yogurt and Mozzarella wheys. This is the first demonstration of increased phage resistance in *S. thermophilus.*

(2) Description Of Related Art

*Lactococcus lactis* and *Streptococcus salivarius* subsp. *thermophilus* cultures are used extensively worldwide in the manufacture of fermented dairy products. The cultures are normally inoculated into pasteurized or heat-treated milk to quickly start and control the fermentation. In this non-sterile milk environment, the added cells come into contact with the wild bacteriophage population that has survived pasteurization. Although natural phage concentration is low, their population increases very rapidly if phage-sensitive cells are present in the starter culture. The consequent lysis of a large number of sensitive cells retards the fermentation process. To cope with this natural phenomenon, the dairy industry has developed a series of solutions including the use of phage resistant *Lactococcus lactis* strains (Hill, C., FEMS Microbiol. Rev. 12: 87–108 (1993)).

*Lactococcus lactis:*

In the last decade, extensive research was conducted on interactions between lactococcal phage and their hosts. *Lactococcus lactis* was found to possess many plasmids coding for natural defense mechanisms against bacteriophages. Over 40 plasmids with phage defense barriers have been identified. Phage resistance systems are classified into three groups based on their mode of action: blocking of phage adsorption, restriction/modification and abortive infection. Phage-resistant *Lactococcus lactis* strains have been constructed by introducing these natural plasmids into phage-sensitive strains (Sanders, M. E., et al., Appl. Environ. Microbiol. 40: 500–506 (1980)). The conjugative abilities of some of these plasmids was exploited to construct such resistant strains (Harrington, A., et al., Appl. Environ. Microbiol. 57: 3405–3409 (1991); Jarvis, A. W., et al., Appl. Environ. Microbiol. 55: 1537–1543 (1988); Sanders, M. E., et al., Appl. Environ. Microbiol. 52: 1001–1007 (1986); and Ward, A. C., et al., J. Dairy Sci. 75: 683–691 (1992)). However, after considerable industrial use of these strains, new phages capable of overcoming the introduced defense mechanism have emerged (Alatossava, T., et al., Appl. Environ. Microbiol. 57: 1346–1353 (1991); Hill, C., et al., J. Bacteriol. 173: 4363–4370 (1991); and Moineau, S., et al., Appl. Environ. Microbiol. 59: 197–202 (1993)). Thus, the search for different natural phage barriers is still an ongoing objective for dairy product starter culture manufacturers.

Over the years several studies have established the heterologous nature of the lactococcal phage population (Jarvis, A. W., et al., Intervirology 32: 2–9 (1991)). Based on electron microscopy and DNA hybridization studies, the Lactococcal and Streptococcal Phage Study Group, which is part of the International Committee on Taxonomy of Viruses, reported the existence of 12 different lactococcal phage species. Recently, this number has been reduced to 10 due to the reclassification of the 1483 and T187 species into the P335 species. Strong DNA homology is observed among members of the same species but no homology is found between species (Braun, V., et al., J. Gen. Microbiol. 135: 2551–2560 (1989); Jarvis, A. W., et al., Intervirology, 32: 2–9 (1991); Moineau, S., et al., Can. J. Microbiol. 38: 875–882 (1992); Powell, I. A., et al., Can. J. Microbiol. 35: 860–866 (1989); and Prevots, F., et al., Appl. Environ. Microbiol. 56: 2180–2185 (1990)). Although many species have been isolated, only three appear to be the most problem for the dairy industry. The species 936 (small isometric head) and c2 (prolate head) have been, by far, the most disturbing lactococcal phage species worldwide. Interestingly, phages from the P335 species (small isometric head) are now being isolated with increasing frequency from North American dairy plants (Moineau, S., et al., Appl. Environ. Microbiol. 59: 197–202 (1993)). Two recent surveys revealed that 100% of the 45 lactococcal phages isolated from Canadian cheese plants and U.S. buttermilk plants were classified within one of these three species: 22 phages belonged to the 936 species, 18 to the c2 species and 5 to the P335 species (Moineau, S., et al., J. Dairy Sci. 77: 18 suppl. 1 (1994); and Moineau, S., et al., Can. J. Microbiol. 38: 875–882 (1992)). Therefore from a practical point of view, industrial *Lactococcus lactis* strains should at least be resistant to the three most common phage species: 936, c2 and P335. Due to the diversity of lactococcal phages, the need for phage defense mechanisms with broad activity (attacking many species) is becoming more meaningful. Because of the characteristics of phages, restriction/modification (R/M) systems have the potential to fulfill this objective.

The phenomenon of R/M was first reported more than 40 years ago (Luria, S. E., et al., J. Bacteriol. 64: 557–569 (1952)) and received a molecular explanation ten (10) years later (Bickle, T. A., et al., Microbiol. Rev. 57: 434–450 (1993); and Dussoix, D., et al., J. Mol. Biol. 5: 37–49 (1962)). The main biological activity of R/M is believed to be in preventing the entrance of foreign DNA (including phage DNA) into the cell. These gatekeepers are roughly the prokaryotic equivalent of the immune system (Wilson, G. G., Nucleic Acids Res. 19: 2539–2566 (1991)). There are currently more than 2400 known restriction enzymes and over 100 have been cloned and sequenced (Raschke, E., GATA 10: 49–60 (1993); and Roberts, R. J., et al., Nucleic Acid Res. 21: 3125–3137 (1993)). There are several kinds of R/M systems and they appear to have equivalent biological activities but achieved in different ways. At least four types of R/M systems have been identified: I, II, IIs, and IIII (Bickle, T. A., et al., Microbiol. Rev. 57: 434–450 (1993); Wilson, G. G., Nucleic Acids Res. 19: 2539–2566 (1991); and Wilson, G. G., et al., Annu. Rev. Genet. 25: 585–627 (1991)). Of these, type II is the simplest and the most common. Illustrative patents are European Patent Application 0 316 677, European Patent Application 0 452 224, U.S. Pat. Nos. 4,530,904 to Hershberger, et al, 4,883,756 to Klaenhammer et al, 4,931,396 to Klaenhammer et al and 5,019,506 to Daly et al.

Many R/M systems have been characterized at the protein level. Restriction enzymes are very dissimilar, suggesting an independent evolution and not from a common ancestor (Bickle, T. A., et al., Microbiol. Rev. 57: 434–450 (1993); Wilson, G. G., Nucleic Acids Res. 19: 2539–2566 (1991); and Wilson, G. G., et al., Annu. Rev. Genet. 25: 585–627 (1991)). In contrast, extensive similarities occur among the methyltransferases (Bickle, T. A., et al., Microbiol. Rev. 57: 434–450 (1993); Klimasauskas, S., et al., Nucleic Acids Res. 17: 9823–9832 (1989); Lauster, R., J. Mol. Biol. 206: 313–321 (1989); McClelland, M., et al., Nucleic Acids Res. 20: 2145–2157 (1992); Wilson, G. G., Nucleic Acids Res. 19: 2539–2566 (1991); and Wilson, G. G., et al., Annu. Rev. Genet. 25: 585–627 (1991)). They can be grouped into three classes corresponding to the modification types: $m^4C$, $m^5C$ and $m^6A$ (Wilson, G. G., Nucleic Acids Res. 19: 2539–2566 (1991); and Wilson, G. G., et al., Annu. Rev. Genet. 25: 585–627 (1991)). $m^4C$ and $m^6A$ can be further divided in two ($\alpha$ and $\beta$) and three ($\alpha$, $\beta$, and $\gamma$) subclasses respectively, based on their amino acid sequences (Klimasauskas, S., et al., Nucleic Acids Res. 17: 9823–9832 (1989); and Lauster, R., J. Mol. Biol. 206: 313–321 (1989)).

A number of plasmids encoding for R/M have been identified in Lactococcus (Hill, C., FEMS Microbiol. Rev. 12: 87–108 (1993)). Surprisingly, only a handful have been partially characterized. The LlaI R/M system encoded on the conjugative plasmid pTR2030, isolated from *Lactococcus lactis* subsp. *lactis* ME2, was the first analyzed at the sequence level (Hill, C., et al., J. Bacteriol. 173: 4363–4370 (1991)). The methylase gene of pTR2030 system has been sequenced and the deduced protein was found to share similarities with the type-IIs methyltransferase ($m^6A$), M. FokI (Hill, C. L., et al., J. Bacteriol. 173: 4363–4370 (1991)). The endonuclease genes have also been sequenced and four open reading frames were identified (O'Sullivan, D. J., et al., FEMS Microbiol. Rev. 12: P100 (1993)). Recent data have provided evidence for a new class of multisubunit endonucleases (O'Sullivan, D. J., et al., FEMS Microbiol. Rev. 12: P100 (1993)). The restriction complex, however, has yet to be purified and its recognition sequence is unknown.

ScrFI was the first classical type II restriction enzyme isolated from *Lactococcus lactis* and is the only one commercially available (Fitzgerald, G. F., et al., Nucleic Acid Research. 10: 8171–8179 (1982)). ScrFI recognizes the sequence 5'-CCNGG-3' where N is any nucleotide. Two methylase genes from the *Lactococcus lactis* subsp. *lactis* UC503 chromosome have been cloned and sequenced (Davis, R., et al., Appl. Environ. Microbiol. 59: 777–785 (1993); and Twomey, D. P., et al., Gene 136: 205–209 (1993)). They both coded for a $m^5C$ MTase. The endonuclease gene has yet to be identified. Mayo et al (Mayo, B., et al., FEMS Microbiol. Lett. 79: 195–198 (1991) isolated a type II endonuclease (also named LlaI) from *L. lactis* subsp. *lactis* NCD0497 which recognized the sequence 5'-CCWGG-3 (W is A or T) but the R/M genes have not been cloned.

Recently Nyengaard, N., et al, Gene 136, 371–372 (1993) described LlaI and LlaBI, which are type II restriction endonucleases from *Lactococcus lactis* subsp. *cremoris* W9 and W56. These endonucleases recognize DNA sequences 5'/GATC-3 and 5'-C/TRYAG3', respectively. The plasmids from these strains were transformed into a plasmid free and endonuclease negative *Lactococcus lactis* subsp. *lactis* by electroporation to produce a transformed strain which resisted phage attack. The DNA was not isolated and sequenced and the natural plasmid was used for the transformation. Further, the authors did not indicate if the plasmids encoded methyl transferase. Strains W9 and W56 were not tested.

*Streptococcus thermophilus:*

Similar information on phage and phage resistance is still very limited for *Streptococcus thermophilus* despite sustained phage infections in the yogurt and Mozzarella cheese industry (Mercenier et al, Genetic engineering of lactobacilli, leuconostocs and *Streptococcus thermophilus,* In M. J. Gasson and W. M. DeVos (ed.), Genetics and biotechnology of lactic acid bacteria. Blackie Acad. Prof. Glaskow, UK p. 253–293 (1994)). Fortunately, *S. thermophilus* phages are much more closely related to each other than the *L. lactis* phages. It appears that there is only one *S. thermophilus* phage species (Mercenier et al Genetic engineering of lactobacilli, leuconostocs and *Streptococcus thermophilus,* In M. J. Gasson and W. M. DeVos (ed.), Genetics and biotechnology of lactic acid bacteria. Blackie Acad. Prof. Glaskow, UK p. 253–293 (1994)). Only very few phage defense mechanisms have been reported for *S. thermophilus.* Four chromosomally-encoded type II R/M systems have been identified in *S. thermophilus.* Solaiman and Somkuti (Solaiman, D. K. Y., et al., FEMS Microbiol. Lett. 67: 261–266 (1990); and Solaiman, D. K. Y., et al., FEMS Microbiol. Lett. 80: 75–80 (1991)) have isolated the endonuclease Sth134I and Sth117I which are isoschizomers of HpaII and EcoRII, respectively. Benbadis et al (Benbadis, L., et al., Appl. Environ. Microbiol. 57: 3677–3678 (1991)) and Guimont et al (Guimont, C., et al., Appl. Microbiol. Biotechnol. 39: 216–220 (1993)) have isolated the endonucleases ssII and Sth455I, respectively. Both are also isoschizomers of EcoRII. In addition, *S. thermophilus* might possess abortive-like phage defense mechanisms (Larbi et al. J. Dairy Res. 59: 349–357 (1992)), although definitive proof has yet to be demonstrated. None of the R/M systems so far identified in *S. thermophilus* have been cloned, sequenced, or used in commercial strains for improvement of phage resistance. There is believed to be no report on improvement of phage resistance of *S. thermophilus* strains.

OBJECTS

It is therefore an object of the present invention to provide an isolated DNA encoding only restriction and modification enzymes to impart phage resistance. Further, it is an object of the present invention to provide transformation vectors and transformed bacteria incorporating the DNA which are particularly useful in the dairy industry. These and other objects will become increasingly apparent by reference to the following description and the drawings.

BRIEF DESCRIPTION OF DRAWINGS

FIGS. 4A to 4C are a nucleotide sequence of the 3-kb NruI-EcoRV fragment from pSRQ700. The deduced amino acid sequence of the 3 ORFs is presented. The putatives promoter, terminator and ribosome binding site are underlined. The first codon of each ORF is in bold. The amino acids are in single letter code.

FIGS. 5A to 5C are charts showing a comparison of the amino acids between A) M.M. LlaIIA (SEQ ID NO. 2), M. DpnII (SEQ ID NO. 5), M.MboA (SEQ ID NO. 6) and E. coli Dam (SEQ ID NO. 7) methylases; B) M.LlaIIB (SEQ ID NO. 3), DpnA (SEQ ID NO. 8), M.MboC (SEQ ID NO. 9) and M.HinfI (SEQ ID NO. 10); C) R.LlaI (SEQ ID NO. 4), R.DpnII (SEQ ID NO. 11) and R.MboI (SEQ ID NO. 12). The asterisk (*) indicates conserved amino acids. Bars show gaps in the aligned sequences.

DESCRIPTION OF PREFERRED EMBODIMENTS

Figure 1:
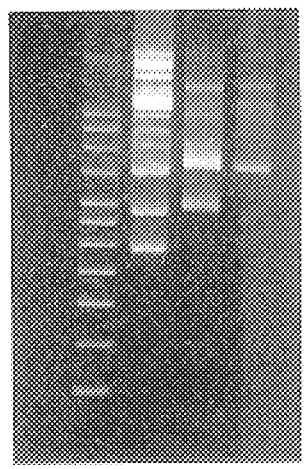
FIG. 1 is an electrophoresis gel showing a plasmid analysis of *Lactococcus lactis* strains wherein Lane 1 is supercoiled DNA ladder (GIBCO/BRL); Lane 2 is *Lactococcus lactis* DCH-4; Lane 3 is *Lactococcus lactis* SMQ-17 (pSA3 and pSRQ700); Lane 4 is *Lactococcus lactis* SMQ-16 (pSA3).

The present invention relates to an isolated DNA encoding only an enzyme which is sufficiently duplicative of a member selected from the group consisting of LlaIIA, LlaIIB and LlaIIC and mixtures thereof to restrict or modify a phage. Further the present invention relates to an isolated DNA having a nucleotide sequence essentially as set forth in SEQ ID NO. 1 selected from the group consisting of ORF1 (positions 97 to 948), ORF2 (positions 941 to 1747) and ORF3 (positions 1740 to 2651) and combinations thereof.

The present invention also relates to a recombinant plasmid containing DNA encoding an enzyme sufficiently duplicative of a member selected from the group consisting of LlaIIA, LlaIIB and LlaIIC and mixtures thereof to restrict or modify a phage.

Further the present invention relates to a bacterium harboring a recombinant plasmid containing DNA encoding for an enzyme sufficiently duplicative of a member selected from the group consisting of LlaIIA, LlaIIB and LlaIIC and mixtures thereof to restrict or modify a phage.

Further still, the present invention relates to a recombinantly produced purified protein which is an enzyme containing a sequence of amino acids sufficiently duplicative of that set forth in a member selected from the group consisting of ORF 1, ORF 2 and ORF 3 and combinations thereof in SEQ ID NO. 2, 3 or 4 such that restriction or modification of a phage can be performed with the enzyme, wherein the protein has been produced from isolated DNA of the SEQ ID NO: 1. The protein can be used for assays as described hereinafter.

Further, the present invention relates to a method of imparting phage resistance to a bacterium which is sensitive to the phage which comprises incorporating recombinant DNA encoding an enzyme sufficiently duplicative of a member selected from the group consisting of LlaIIA, LlaIIB and LlaIIC and mixtures thereof into the bacterium to impart the phage resistance, wherein the DNA encoding the member is contained in strain Lactococcus lactis SMQ-17 deposited as NRRL-B-21337. Preferably the bacterium is a dairy culture. In particular, the present invention relates to a bacterium, preferably isolated and purified, selected from the group consisting of Streptococcus salivarius subsp. thermophilus and Lactococcus lactis naturally lacking in phage resistance which bacterium contains recombinant DNA encoding for an enzyme sufficiently duplicate of a member selected from the group consisting of LlaIIA, LlaIIB and LlaIIC and having a sequence of the DNA for the member is essentially as set forth in SEQ ID NO: 1 to impart phage resistance.

Finally, the present invention relates to a method for fermenting a dairy product, the improvement which comprises using a dairy culture selected from the group consisting of Lactococcus lactis and Streptococcus salivarius subsp. thermophilus incorporating recombinant DNA encoding for an enzyme sufficiently duplicative of a member selected from the group consisting of LlaIIA, LlaIIB and LlaIIC to impart phage resistance, wherein the DNA for the member is contained in strain Lactococcus lactis SMQ-17 deposited as NRRL-B-21337. The DNA is generally transformed into the dairy culture.

The DNA of SEQ ID NO: 1 and FIGS. 4A to 4C (Appendix I) is contained in Lactococcus lactis SMQ-17 deposited under the Budapest Treaty on Sep. 29, 1994 as NRRL-B-21337. The strain is available upon request by name and deposit number. The isolated DNA is obtained by means of EcoRV or NruI-TcoRV digestion of pSRQ700 as described hereinafter.

The art of DNA isolation and cloning is well known to those skilled in the art. Further, the terminology of this art is well developed, see for instance EP 0316677 A2. As used herein, the term "transformed" means to transfer DNA from one bacterium to another in related bacterium. The term "recombinant" as used herein means DNA in a form not existing in nature. In general the recombinant DNA contains DNA encoding only one or more of the sequence of amino acids for LlaIIA, LlaIIB and LlaIIC as set forth in SEQ ID NO: 1. The recombinant enzymes encoded are like the natural enzymes except that the physical configurations are different and they are thus different. They retain the ability to restrict or modify (methylate) the phage DNA.

Various shuttle vectors can be used. pSA3 from Dao, M., et al., Applied Environ. Microb. 49: 115–119 (1985) was used.

The recombinant bacterium can be for instance Escherichia coli, a Lactococcus sp. or a Streptococcus sp. used in dairy fermentations. The E. coli are used to produce the enzymes of SEQ ID NO: 2, 3 and/or 4 which can be used to produce a DNA or RNA probe in a known manner or can be used to produce antibodies to the enzymes in a well known manner for use in assays for the enzymes. Purification of the enzymes is achieved using affinity chromatography and/or molecular filtration.

The DNA of SEQ ID NO: 1 can have modifications in sequence and still be homologous and still encode enzymes which have the necessary phage resistance properties. Generally within 75–100% homology is sufficient.

The preferred use of the transformed cultures containing the recombinant DNA of SEQ ID NO: 1 is in dairy product fermentations. Such fermentations are well known to those skilled in the art. The preferred strains are transformed Lactococcus lactis and Streptococcus salivarius sp. thermophilus which are used in the dairy product fermentations.

EXAMPLE 1

Bacterial Strains, Plasmids, and Media

The strains and plasmids and enzymes used in this invention are listed in Tables 1 and 2.

TABLE 1

Bacterial strains, plasmids and bacteriophages.

| Bacteria, plasmids, and phages | Relevant characteristics | Source |
|---|---|---|
| *L. lactis* subsp. *cremoris* | | |
| DCH-4 | Industrial strain, multiple plasmids, Lac+ | Invention |
| UL8 | Industrial strain, host for P335 phages, Lac+ | Moineau, S., et al., Can J. Microbiol. 38: 875–882 (1992) |
| SMQ-87 | UL8 (pSRQ701), Lac+, Em$^r$ | Invention |
| *L. lactis* subsp. *lactis* | | |
| LM0230 | Plasmid free, host for 936 and c2 phages, Lac− | McKay, L. L., et al, Appl. Environ. Microbiol. 23:1090–1096 (1972) |
| SMQ-16 | LM0230 (pSA3), Lac−, Em$^r$. | Invention |
| SMQ-17 | LM0230 (pSA3, pSRQ700), Lac−, Em$^r$ | Invention |
| SMQ-39 | LM0230 (pSRQ701), Lac−, Em$^r$ | Invention |
| SMQ-40 | LM0230 (pSRQ702), Lac−, Em$^r$ | Invention |
| SMQ-50 | LM0230 (pSRQ703), Lac−, Em$^r$ | Invention |
| SMQ-117 | LM0230 (pSRQ704), Lac−, Em$^r$ | Invention |
| SMQ-140 | LM0230 (pSRQ706), Lac−, Em$^r$ | Invention |
| *E. coli* | | |
| DH5α | Transformation host | GIBCO/BRL (Grand Island, NY) |
| DMQ-149 | DH5α (pSRQ708), Ap$^r$ | Invention |
| Pages | | |
| Øp2 | Small isometric headed, 936 species, 30.5 kb | L. L. McKay |
| Øsk1 | Small isometric headed, 936 species, 28.1 kb | L. L. McKay |
| Øjj50 | Small isometric headed, 936 species, 30.5 kb | J. Josephsen, et al., FEMS Microbiol. Lett. 59:161–166 (1989) |
| Øc2 | Prolate headed, c2 species, 20.7 kb | Sanders, M. E., et al., Appl. Environ. Microbiol. 40:500–506 (1980) |
| Øm13 | Prolate headed, c2 species, 20.2 kb | W. E. Sandine |
| Øeb1 | Prolate headed, c2 species, 19.6 kb | L. L. McKay |
| Øu136 | Small isometric headed, P335 species, 28.8 kb | Moineau, S., et al., Can J. Microbiol. 38: 875–882 (1992) |
| ØQ30 | Small isometric headed, P335 species, 37.0 kb | Moineau, S., et al., J. Dairy Sci. 77:18 Suppl. 1 (1994) |
| ØQ33 | Small isometric headed, P335 species, 29.6 kb | Moineau, S., et al., J. Dairy Sci. 77:18 Suppl. 1 (1994) |

L. L. McKay, University of Minnesota; W. E. Sandine, Oregon State University; Lac, lactose-fermenting ability; Ap$^4$, ampicillin resistance; Cm$^r$, chloramphenicol resistance; Em$^r$, erythromycin resistance.

TABLE 2

Plasmids used in this study.

| Plasmid | Relevant characteristics | Source |
|---|---|---|
| pSA3 | Shuttle vector, Cm, Tc, Em, 10.2 kb. | Dao, M. L., et al., Appl. Env. Microb. 49:115–119 (1985) |
| pBS KS(+) | Cloning vector for sequencing, Ap, 2.9 kb. | Stratagene |
| pSRQ700 | Resident plasmid of DCH-4, R+/M+, 7.8 kb. | This study |
| pSRQ701 | 7.0-kb EcoRI fragment from pSRQ700 cloned into pSA3, R+/M+, Cm$^s$, Tc$^r$, Em$^r$. | This study |
| pSRQ702 | 5.3-kb NcoI-EcoRI fragment from pSRQ700 cloned into pSA3, R−/M+, Cm$^s$, Tc$^r$, Em$^r$. | This study |
| pSRQ703 | 6.6-kb NcoI fragment from pSRQ700 cloned into pSA3, R−/M+, Cm$^s$, Tc$^r$, Em$^r$. | This study |
| pSRQ704 | 7.8-kb EcoRV fragment from pSRQ700 cloned into pSA3, R+/M+, Cm$^r$, Tc$^s$, Em$^r$. | This study |
| pSRQ706 | 3.0-kb NruI-EcoRV fragment from pSRQ700 cloned into pSA3, R+/M+, Cm$^r$, Tc$^s$, Em$^r$. | This study |
| pSRQ708 | 3.0-kb NruI-EcoRV fragment from pSRQ700 cloned into pBS, R+/M+, Ap$^r$. | This study |

Ap$^r$, ampicillin resistance; Cm$^r$, chloramphenicol resistance; Cm$^s$, sensitive to chloramphenicol; Em$^r$, erythromycin resistance; Tc$^r$, tetracycline resistance; Tc$^s$, tetracycline resistance; R+/M+, active restriction/active modification enzymes;

*Escherichia coli* was grown at 37° C. in Luria-Bertani (Sambrooke, J., et al., Molecular cloning: a laboratory manual. 2nd ed. Cold Spring Harbor Laboratory, Cold Spring Harbor, N.Y. (1989)). *Lactococcus lactis* strains were grown at 30° C. in M17 (Terzaghi, B. E., et al., Appl. Microbiol. 29: 807–813 (1975)) supplemented with 0.5% glucose (GM17) or 0.5% lactose (LM17). When appropriate, antibiotics were added as follows: for *E. coli*, 50 μg/ml of ampicillin (Ap), 10 μg/ml of tetracycline (Tc), and 20 μg/ml of chloramphenicol (Cm); for *L. lactis*, 5 μg/ml of erythromycin (Em).

Bacteriophage Propagation and Assays

Bacteriophages used in this invention are listed in Table 1. Bacteriophages were propagated and titrated by the method of Jarvis (Jarvis, A. W., Appl. Environ. Microbiol. 36: 785–789 (1978)). Efficiency of plaguing (EOP) assays were performed as described by Sanders and Klaenhammer (Sanders, M. E., et al., Appl. Environ. Microbiol. 40: 500–506 (1980)). Bacteriophages c2, p2, sk1 and jj50 were supplied by T. R. Klaenhammer (North Carolina State University).

DNA Isolation and Manipulation

Plasmid DNA from *E. coli* was isolated as described previously (Moineau, S., et al., Appl. Environ. Microbiol. 60: 1832–1841 (1994)). Large quantities of *E. coli* plasmid DNA was isolated by using plasmid MIDI or MAXI kit (Qiagen Inc., Chatsworth, Calif.). Plasmid DNA from *L. lactis* was isolated as described by O'Sullivan and Klaenhammer (O'Sullivan, D. J., et al., Appl. Environ. Microbiol. 59: 2730–2733 (1993)). Large quantity of lactococcal plasmid DNA was obtained using the Leblanc and Lee procedure (Leblanc, D. J., et al., J. Bacteriol. 140: 1112–1115 (1979)) as modified by Gonzalez and Kunka (Gonzalez, C. F., et al., Appl. Environ. Microbiol. 46: 81–89 (1983)). Restriction endonucleases (Gibco/BRL, Grand Island, N.Y.)

and T4 DNA ligase (Boehringer Manheim, Indianapolis, Ind.) were used according to manufacturer's instructions. When needed, DNA fragments were obtained from low-melting agarose using a QIAEX gel extraction kit (Qiagen, Inc., Chatsworth, Calif.).

Electroporation

E. coli was grown, electroporated, incubated, and plated as described previously (Moineau, S., et al., Appl. Environ. Microbiol. 60: 1832–1841 (1994)). L. lactis was grown in GM17 supplemented with 0.5 M sucrose (SGM17) and 1% glycine and electroporated as described by Holo and Nes (Holo, H., et al., Appl. Environ. Microbiol. 55: 3119–3123 (1989)). The Gene Pulser apparatus (Bio-Rad Laboratories, Richmond, Calif.) was set at 25 µF and 2.45 kV, and the Pulse Controller was set at 200 Ω. Plasmid DNA was mixed with 40 µl of cells in a chilled cuvette (0.2 cm). After electroporation, L. lactis cells were resuspended in SGM17, incubated for 2 h at 30° C., plated on GM17 supplemented with erythromycin (5 µg/ml) and incubated for 2 days at 30° C.

Sequencing

The entire LlaII system (3 kb NruI-EcoRV fragment from pSRQ700) was cloned into E. coli pBluescript. The resulting clone was named pSRQ708. Nested deletions were made in both orientations from pSRQ708 using the ERASE-A-BASE kit (Promega, Madison, Wis.). For the first set of deletions, the endonucleases SstI was used for protection and XbaI to start the deletion. The restriction pairs KpnI-DraII were used to obtain the nested deletions in the other orientation. Plasmid DNA was extracted from the nested clones with QIAGEN and directly used for sequencing. The sequencing reactions were performed using the DYEDEOXY TERMINATOR TAQ sequencing kit for use on the 373A automated DNA sequencing system (Applied Biosystems, Foster City, Calif.). The T7 and T3 primers were used for annealing.

Restriction enzyme purification

L. lactis SMQ-17 was grown in 2L, concentrated by centrifugation (10,000 rpm, 15 min.) and washed twice in saline. The cells were then resuspended in 30 ml of PME buffer (10 mM $NaH_2PO_4$ pH 7.4, 0.1 mM EDTA and 10 mM β-mercaptoethanol). Cells were lysed by 15 bursts (30 seconds each followed by one minute rest) with glass beads and a bead beater (BIOSPEC, Bartlesville, Okla.). After centrifugation to remove cell debris and glass beads, the supernatant was used for ion exchange chromatography. Successive chromatographies were performed on phosphocellulose (Whatman P11, Maidstone, England) and dimethylaminoethyl cellulose (Whatman DE5, Maidstone, England) using a salt gradient in PME buffer. Restriction endonuclease activity was found in the fractions around 0.5 M NaCl. Lactococcal phage ul36 DNA was used as substrate and the digestions were performed at 37° C. for 2–4 h using the buffer system #2 from GIBCO/BRL (50 mM Tris-HCl pH 8.0, 10 mM $MgCl_2$, 50 mM NaCl). DNA samples were analyzed as described by Sambrooke et al in Molecular cloning: a laboratory manual, 2nd ed. Cold Spring Harbor Laboratory, Cold Spring Harbor, N.Y. (1989) in 0.7% agarose gels in TAE.

DNA and Protein Analysis

The DNA sequence was analyzed with DNA strider 1.2. The SwissProt database (release 29, Jun. 1994) was searched for homology to all three LlaII amino acid sequences of SEQ ID NO: 1.

Isolation of pSRQ700

For many years, Lactococcus lactis subsp. cremoris DCH-4 has performed very well during the industrial buttermilk and sour cream production. One reason for continued good performance is the natural resistance of DCH-4 to lactococcal bacteriophages. One objective of this invention was to identify and transfer the DNA responsible for the phage resistance of DCH-4. The total plasmid DNA of DCH-4 was isolated and co-electroporated with the vector pSA3 into the phage sensitive-plasmid free L. lactis LM0230. The latter strain was selected because it can propagate phages from two species, 936 and c2. The DNA ratio of DCH-4:pSA3 used for electroporation was about 10:1. Em-resistant colonies were tested for phage resistance by spot assay ($10^3$–$10^4$ pfu of Øp2/spot). A few phage resistant colonies were obtained, analyzed, and found to contain pSA3 and a 7.8 kb low copy plasmid which was named pSRQ700 (FIG. 1). The transformant containing pSRQ700 was named L. lactis SMQ-17 (NRRL-B-21337). Plasmid pSRQ700 was also electroporated into L. lactis UL8 which can propagate phages from the P335 species. The transformant was named L. lactis SMQ-87.

Effectiveness of pSRQ700 on lactococcal Phage Species

L. lactis SMQ-17 and SMQ-87 were tested for phage resistance against a total of 9 phages belonging to 3 species (3 phages/species). Phages p2, sk1 and jj50 were selected as representatives of the 936 species (Table 1). The lactococcal phage species c2 was represented by the phages c2, ml3 and eb1. These six phages were individually tested on SMQ-17 and their EOPs are presented in Table 3.

TABLE 3

Comparison between the efficiency of plaquing of lactococcal phages on L. lactis SMQ-17 and the number of MboI sites in the phage genome.

| | EOP on SMQ-17 | Number of MboI sites* |
|---|---|---|
| 936 species | | |
| øp2 | $1.7 \times 10^{-6}$ | 11 |
| øsk1 | $2.5 \times 10^{-6}$ | 9 |
| øjj50 | $2.0 \times 10^{-6}$ | 10 |
| c2 species | | |
| øc2* | $1.0 \times 10^{-4}$ | 3 |
| øml3 | $6.1 \times 10^{-3}$ | 2 |
| øeb1 | $5.5 \times 10^{-3}$ | 2 |
| P335 species | | |
| øul36 | $2.7 \times 10^{-7}$ | 13 |
| øQ30 | $5.2 \times 10^{-6}$ | 12 |
| øQ33 | $1.3 \times 10^{-7}$ | 15 |

*Only number of fragments > 0.5 kb were determined.

The new emerging P335 species was represented by the phages ul36, Q30 and Q33. They were tested separately on SMQ-87 and their EOPs are also presented in Table 3. All three 936 phages had similar EOPs in the range of $10^{-6}$. More variability was observed with the c2 species where EOPs ranged from $10^{-3}$ to $10^{-4}$. The P335 phages were the most affected by pSRQ700 since EOPs of $10^{-7}$ were observed (Table 3). Identical results were obtained when phage resistance was tested at 21°, 30° and 38° C. (data not shown). These results indicated that the phage resistance mechanism encoded on pSRQ700 is temperature insensitive.

Identification of the Phage Resistance Mechanism on pSRQ700

Phages capable of overcoming the defense mechanism encoded on pSRQ700 were isolated. These phages had EOPs of 1.0 on *L. lactis* SMQ-17. When these resistant (modified) phages were propagated back on their original host, they became sensitive (restricted) to pSRQ700 at the same previous level (data not shown). This temporary host specific immunity, demonstrates the presence of a classical R/M system encoded on pSRQ700. The R/M system was named LlaII.

Isolation of the Restriction Endonuclease

The non-specific nucleases were removed after ion exchange chromatographies performed on phosphocellulose (Whatman P11) and dimethylaminoethyl cellulose (Whatman DE5) using a salt gradient in PME (10 mM $NaH_2PO_4$ pH 7.4, 0.1 mM EDTA and 10 mM β-mercaptoethanol) buffer. DNAs from the well-characterized lactococcal phage ul36 (Moineau, S., et al., Can. J. Microbiol. 38: 875–882 (1992: Moineau, S., et al., Appl. Environ. Microbiol. 59: 197–202 (1993); and Moineau, S., et al., Appl. Environ. Microbiol. 60: ;1832–1841 (1994)) was digested with LlaII. The digestions were conducted overnight at 37° C. since the R/M encoded on pSRQ700 is temperature-insensitive (up to 38° C.). Defined DNA fragments were identified on agarose gels (data not shown). No attempts were made to determine the number of activity units in the collected fractions nor the percentage of recovery from the crude supernatant. Unexpectedly, the restriction patterns obtained corresponded to MboI restriction patterns. Attempts to cut pSRQ700 with MboI were unsuccessful. It was concluded that the R/M system present on pSRQ700 was similar to the MboI system which recognized the sequence 5'-GATC-3' and cleaved it before the guanine.

Mapping of pSRQ700

Figure 2:
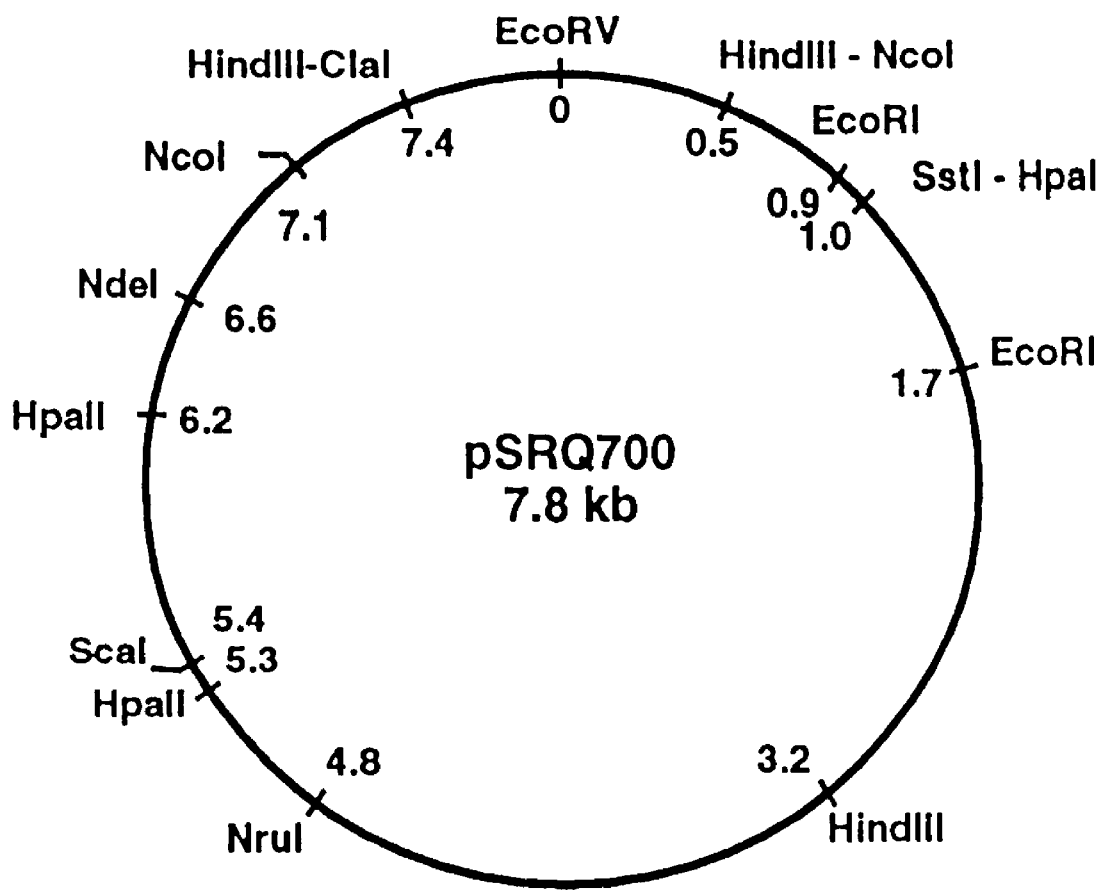
FIG. 2 is an endonuclease restriction map of lactococcal plasmid pSRQ700. Site positions are indicated in kb.

Single, double and triple digestions were performed with endonucleases to obtain a map of pSRQ700. The results are presented in FIG. 2. The following endonucleases did not cut pSRQ700: ApaI, AvaI, AvaII, BalI, BamHI, HpaI, MboI, PstI, PvuII, SalI, SmaI, SphI, XbaI, XhoI.

Localization of the LlaII System on pSRQ700

Figure 3:
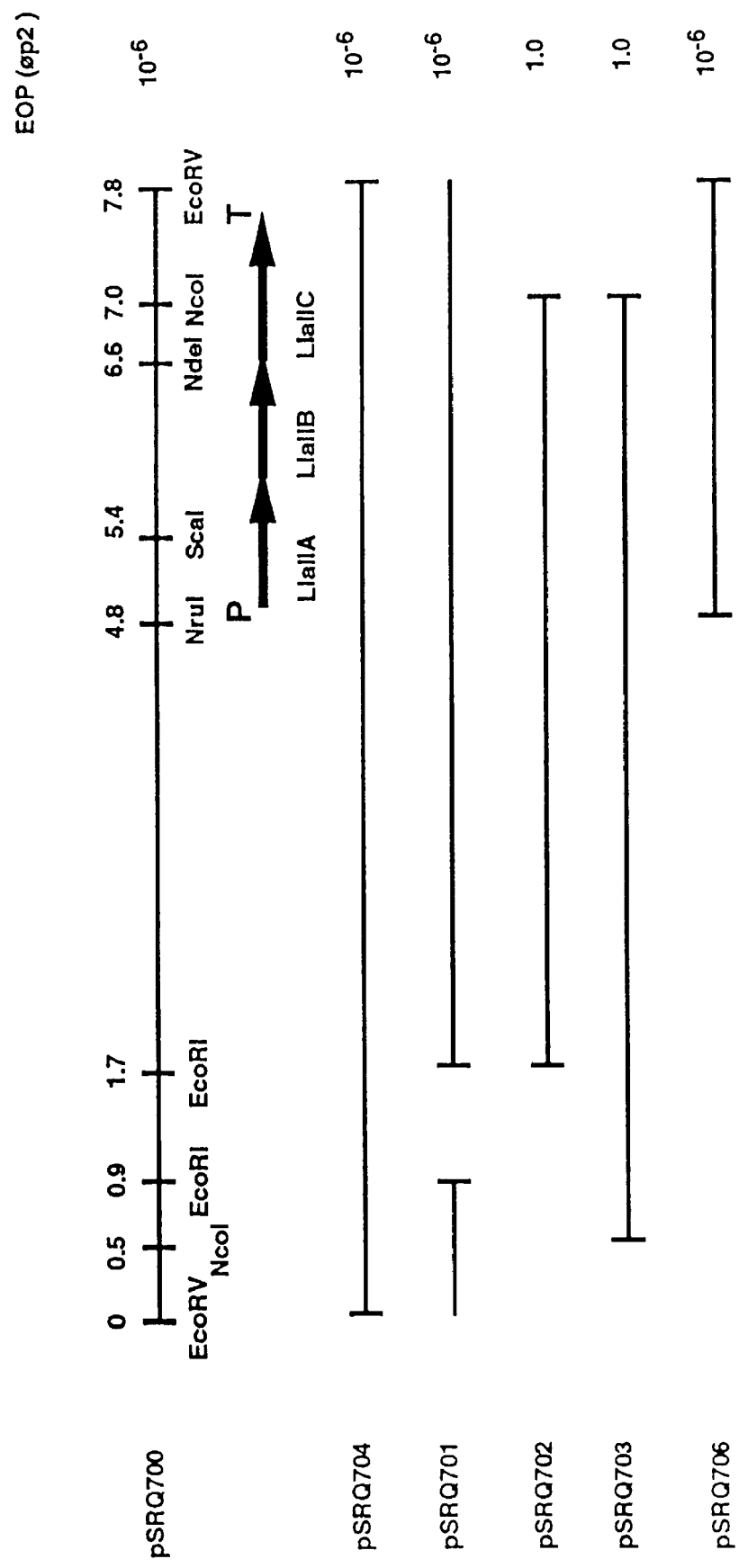
FIG. 3 is a map showing cloning of LlaII from pSRQ700 into pSA3. Clones were electroporated into LM0230. Transformants were tested for phage resistance against Øp2.

The LlaII R/M system was entirely cloned into *E. coli* using the *E. coli-L. lactis* shuttle vector pSA3 (FIG. 3). Since appropriate unique restriction sites were present on PSA3 and PSRQ700, total plasmid DNA from *L. lactis* SMQ-17 was directly used for cloning. Plasmid DNA from SMQ-17 was digested with selected endonucleases, phenol extracted, ethanol precipitated, ligated and the ligation mixture electroporated in *E. coli* DH5α. This strategy was very effective because expected clones were rapidly obtained. The clones were electroporated into *L. lactis* LM0230 and phage resistance was determined. The relevant clones are presented in FIG. 3. The entire R/M system of PSRQ700 was localized on a 3-kb NruI-EcoRV fragment. The PSA3 clone containing this 3 kb fragment was named pSRQ706. Similar EOPs were obtained with PSRQ700 and PSRQ706 (FIG. 3). This is due to the similar low copy number of PSA3 and PSRQ700 (FIG. 1).

DNA Sequence Analysis of the LlaII

The 3-kb NruI-EcoRV fragment containing the LlaII genes was sequenced in both directions and found to contain 2,987 bp (FIGS. 4A to 4C; SEQ ID NO: 1). This fragment was 65.7% A+T rich, typical of lactococcal genes (Van de Guchte, M., et al., FEMS Microbiol. Rev. 88: 73–92 (1992)).

Three overlapping open reading frames (orfs) were found and the genes were named LlaIIA, LlaIIB and LlaIIC. In reference to FIGS. 4A to 4C and SEQ ID NO: 1, the gene LlaIIA was localized from position 97 to position 948 and coded for a protein of 284 amino acids with an estimated weight of 33,031 Da. The gene LlaIIB was localized from position 941 to position 1747 and coded for a protein of 269 amino acids with an estimated weight of 30,904 Da. The gene LlaIIC was localized from position 1740 to position 2651 and coded for a protein of 304 amino acids with an estimated weight of 34,720 Da. Phage p2 EOP of 1.0 on *L. lactis* harboring pSRQ702 or pSRQ703 suggested that LlaIIC coded for the endonuclease (FIG. 3). No putative ribosome binding site (RBS) was found for LlaIIA and LlaIIB. A putative RBS (GGAG) was found preceding LlaIIC. Atypical RBS have been identified for the DpnII methylases which are similar to LlaII (FIGS. 5A to 5C). They were not found in the LlaII system. Atypical RBS may be related to translational control of the methylase gene expression (Lacks, S. A., et al., In: Genetics and Molecular Biology of Streptococci, Lactococci and Enterococci, Dunny, G. M., P. P. Cleary and L. L. McKay. (eds) ASM, Washington , D.C. p.71–76 (1991)). All three genes appear to be under the control of the same promoter. However, no definite consensus *E. coli*-10 and -35 promoter sequences could be identified. Because EOPs were the same in PSRQ700, pSRQ701 and PSRQ703 (FIG. 3), it is believed that the promoter was present in the 3.0-kb fragment. The putative promoter sequences upstream of LlaIIA is of interest. A putative -35 region was localized at position 27, followed by a 18 bp spacer, and a putative -10 region at position 51 (FIGS. 4A to 4C). A search for palindromic sequences identified two perfect inverted repeats of 19 bp, typical of a strong rho-independent terminator, at the very end of LlaIIC (FIGS. 4A to 4C). Interestingly, the stop codon of LlaIIC was within the beginning of the stemloop structure.

Protein Analysis

Homology searches showed that the deduced protein coded by LlaIIA was 75.4% identical to DpnII methylase (Mannarelli, B. M., et al., Proc. Natl. Acad. Sci. 82: 4468–4472 (1985)), 41.5% identical MboI methylase (Ueno, T., et al., Nucleic Acids Res. 10: 2309–2313 (1993)) and 30.1% to the Dam methylase of *E. coli* (Brooks, J. E., et al., Nucleic Acids Res. 11: 837–851 (1983)). It was concluded that LlaIIA codes for a methylase and was named M.LlaIIA. All three methylases (M.DpnII, M.MboA and Dam) homologous to LlaIIA are N-6 adenine methyltransferase ($m^6$A-MTases). The most conserved amino acid sequence motifs among the $m^6$A-Mtases are F-G-G (motif I) and DPPY (motif II). Their organization in the protein allowed the division of the $m^6$A-Mtases in three subclasses (α, β and γ). In the $m^6$A-Mtase subclass α, the motif I is found close to the N-terminal followed by a variable region of 100–200 aa and the motif II close to the C-terminal. The reverse situation is found in the subclass β, where the motif II appears before the motif I. M.LlaIIA has all the characteristics of a $m^6$A-Mtase subclass a: F-G-G motif, a 146 aa variable region and a DPPY motif (FIG. 5). The F-G-G motif probably contained the S-adenosylmethionine binding site and DPPY might be involved in the methylation of exocyclic amino acids (Klimasauskas, S., et al., Nucleic Acids Res. 17: 9823–9832 (1989)).

The deduced protein coded by LlaIIB was found to be 88.9% identical to the second methylase of DpnII (Cerritelli, S., et al., Proc. Natl. Acad. Sci. USA, 86: 9223–9227

(1989)), 50.2% identical to the second methylase of MboI (Ueno, T., et al., Nucleic Acids Res. 10: 2309–2313 (1993)) and 43.6% identical to the HinfI methylase (Chandrasegaran, S., et al., Gene 70: 387–392 (1988)). It was concluded that LlaIIB also codes for a methylase and was named M.LlaIIB. All three methylases (M.DpnA, M.MboC and HinfI) homologous to LlaIIB are $m^6$A-Mtases but subclass β. M.LlaIIB has all the subclass β characteristics: a DPPY motif, a 175 aa variable region and a F-G-G motif. Interestingly, FIGS. 5A to 5C also show the amino acid comparison between two sets of four $m^6$A-Mtases isolated from two Gram-positive and two Gram-negative bacteria. This enzyme methylates the same 5'-GATC-3' sequence. Despite the various origins, about 20% and 28% of the amino acids are respectively conserved in the four α and β methylases studied. Interestingly, almost all tryptophan residues are conserved in the methylases studied (FIGS. 5A to 5C).

The deduced protein coded by LlaIIC was 34% and 31% identical to MboI (Ueno, T., et al., Nucleic Acids Res. 10: 2309–2313 (1993)) and DpnII (de la Campa, A. G., et al., J. Biol. chem. 263: 14696–14702 (1987)) endonucleases, respectively. These results confirmed that LlaIIC coded for an endonuclease and was named R.LlaII. Conserved aa motifs were observed among the three isoschizomers but their functionality is unknown.

It was thus found that *Lactococcus lactis* subsp *cremoris* DCH-4 harbors a 7.8-kb low copy plasmid (PSRQ700) coding for a temperature-insensitive R/M system similar to DpnII (Lacks, S. A., et al., In: Genetics and Molecular biology of Streptococci, Lactococci and Enterococci. Dunny, G. M., P. P. Cleary and L. L. McKay. (eds) ASM, Washington , D.C. p-71-76 (1991)) and MboI (Ueno, T., et al., Nucleic Acids Res. 10: 2309–2313 (1993)). These systems recognize the non-methylated DNA sequence 5'-GATC-3' where the endonuclease cleaved before the guanine (Lacks, S. A., et al., In: Genetics and Molecular biology of Streptococci, Lactococci and Enterococci. Dunny, G. M., P. P. Cleary and L. L. McKay. (eds) ASM, Washington , D.C. p-71-76 (1991); and (Ueno, T., et al., Nucleic Acids Res. 10: 2309–2313 (1993)). The plasmid PSRQ700 is probably one reason for the strong phage resistance shown by DCH-4 over the years. Any phage containing the non-methylated GATC sequence in its genome will be restricted when infecting a *L. lactis* strain containing PSRQ700.

Members of the three most common lactococcal phage species were strongly restricted by PSRQ700 as shown by their reduced EOPs (Table 3). The small isometric-headed phages of the P335 and 936 species were particularly affected by PSRQ700. This is due in part to their larger genomes. The average genome size for the P335, 936 and c2 phages used in this study was 31.8, 29.7 and 20.2-kb, respectively. However, the most important factor was the number of LlaII sites in the phage genome. Three LlaII sites in the prolate Øc2 genome were enough to restrict its EOP by 4 logs on *L. lactis* SMQ-17 (Table 3). Two LlaII sites in the Øml3 and Øeb1 genomes were still enough to reduce the EOP by 3 logs. These data are in agreement with the single hit kinetic of R/M system and shows that restriction at one site is enough to prevent phage proliferation (Wilson, G. G., et al., Annu. Rev. Genet. 25: 585–627 (1991)). For the small isometric phages which had more LlaII sites in their genome, the presence of 9 to 12 sites gave a 6 log reduction in EOP, whereas 13 to 15 sites were needed for a 7 log reduction. As reported previously, the EOP decreases logarithmically as the number of sites in the phage genome increases (Wilson, G. G., et al., Annu. Rev. Genet. 25: 585–627 (1991)).

Thus, phage resistance conferred by PSRQ700 was substantial against members of the 3-lactococcal phage species tested.

Close gene linkage is a feature of all R/M system and accordingly LlaII genes are adjacent (Wilson, G. G., Nucleic Acids Res. 19: 2539–2566 (1991); and Wilson, G. G., et al. Annu. Rev. Genet. 25: 585–627 (1991)). The LlaII system is highly related to DpnII (Lacks, S. A., et al., In: Genetics and Molecular Biology of Streptococci, Lactococci and Enterococci. Dunny, G. M., P. P. Cleary and L. L. McKay. (eds) ASM, Washington, D.C. p. 71–76 (1991)). They share the same genetic structure: two methylases followed by an endonuclease (de la Campa, A. G., et al., J. Mol. Biol. 196: 457–469 (1987)). There is also gene overlapping in both systems. The most striking similarity is their methylases (Cerritelli, S., et al., Proc. Natl. Acad. Sci. USA. 86: 9223–9227); and Mannarelli, B. M., et al., Proc. Natl. Acad. Sci. 82: 4468–4472 (1985)). Amino acids comparison showed 75% identity between M.LlaIIA and M.DpnII and 88% between M.LlaIIB and M.DpnA (FIG. 5).

Despite the strong homology between LlaII and DpnII methylases, the endonucleases are still divergent. Only 31% of the amino acids are identical. In fact, the endonuclease of LlaII is more homologous to MboI than to DpnII. One might suggest that the methylase had a common ancestor whereas endonucleases evolved independently (Bickle, T. A., et al., Microbiol. Rev. 57: 434–450 (1993); (Wilson, G. G., Nucleic Acids Res. 19: 2539–2566 (1991); and Wilson, G. G., et al. Annu. Rev. Genet. 25: 585–627 (1991)). Many type II R/M system appear to have formed partnerships with miscellaneous genes that were initially separated. They became linked due to a persistent selective advantage (Bickle, T. A., et al., Microbiol. Rev. 57: 434–450 (1993); (Wilson, G. G., Nucleic Acids Res. 19: 2539–2566 (1991); and Wilson, G. G., et al. Annu. Rev. Genet. 25: 585–627 (1991)).

Finally, from a culture manufacturer standpoint, the introduction of the natural low copy number PSRQ700 into industrial *Lactococcus lactis* strains can confer strong phage resistance against phages of the 936 species and the newly emerging P335 species. Its effectiveness against c2 species will be variable. The temperature insensitivity nature of LlaII (up to 38° C.) makes this phage resistance mechanism amenable to various types of high-temperature dairy fermentations, especially cheese. The use of PSRQ700 as part of a starter rotation scheme (to avoid the build up of modified phages) can improve the overall phage resistance of starter cultures.

EXAMPLE 2

The native LlaII R/M system from *Lactococcus lactis* was expressed by and conferred strong phage resistance to various industrial *S. thermophilus* strains. Resistance was observed against phages isolated from yogurt and Mozzarella wheys.

Bacteria, Bacteriophages, and Media

The strains used in this study are listed in Table 4. *S. thermophilus* strains were confirmed by Rapid ID 32 Strep (BioMérieux Vitek, Inc., Hazelwood, Mo.). *Streptococcus thermophilus* strains were grown at 42° C. in GM17. When needed, antibiotics were added at 5 μg of chloramphenicol per ml. Bacteriophages used in this study are listed in Table 4.

TABLE 4

Bacteria and bacteriophages used in this study.

| Bacteria or phage | Relevant characteristics[a] | Source |
|---|---|---|
| *E. coli* | | |
| DH5α | Transformation host. | Gibco/BRL |
| *L. lactis* | | |
| LM0230 | Plasmid-free, Lac−, host for øp2. | 38 |
| SMQ-17 | LM0230 (pSRQ700). | This Invention |
| SMQ-151 | LM0230 (pSRQ707), Cm[r]. | This Invention |
| *S. thermophilus* | | |
| SMQ-119 | Industrial strain used in yogurt, host for øQ1 and øQ3. | This Invention |
| SMQ-146 | SMQ-119 (pNZ123), Cm[r]. | This Invention |
| SMQ-154 | SMQ-119 (pSRQ707), Cm[r]. | This Invention |
| SMQ-173 | Industrial strain used for Mozzarella, host for øQ5. | This Invention |
| SMQ-174 | Industrial strain used for Mozzarella, host for øQ6. | This Invention |
| SMQ-211 | SMQ-173 (pSRQ707), Cm[r]. | This Invention |
| SMQ-212 | SMQ-174 (pSRQ707), Cm[r]. | This Invention |
| Phages | | |
| øp2 | *L. lactis* phage, small isometric-head, 936 species. | L. L. McKay |
| øQ1 | *S. thermophilus* phage isolated from yogurt. | This Invention |
| øQ3 | *S. thermophilus* phage isolated from yogurt. | This Invention |
| øQ5 | *S. thermophilus* phage isolated from Mozzarella whey. | This Invention |
| øQ6 | *S. thermophilus* phage isolated from Mozzarella whey. | This Invention |

L. L. McKay, University of Minnesota; Cm[r], chloramphenicol resistance; Lac−, deficient in lactose fermenting ability.

Streptococcal phages were propagated by the method of Jarvis et al (Jarvis, A. W., et al., Intervirology 32: 2–9 (1991)). EOP assays on *S. thermophilus* hosts were performed as follows: strains were grown in GM17 overnight at 37 C., 500 μl of cells and 100 μl of diluted phages were mixed with 2.5 ml of soft agar (GM17 supplemented with 10 mM CaCl$_2$) and layered onto bottom agar (GM17+CaCl$_2$) Plates were incubated overnight 42° C. in an anaerobic jar (BBL GasPaK Plus, Beckton Dickinson, Cockeysville, Md.).

DNA Isolation and Manipulation

Plasmid DNA from *S. thermophilus* was isolated by using the method of O'Sullivan and Klaenhammer (O'Sullivan, D. J., et al., Appl. Environ. Microbiol. 59: 2730–2733 (1993)). Phage DNA was isolated as described previously (Moineau, S., et al., Appl. Environ. Microbiol. 60: 1832–1841 (1994)).

Electroporation

*S. thermophilus* cells were electroporated as follows: cells were grown in GM17 until mid-exponential phase, centrifuged, washed twice with SG buffer (0.5 M sucrose and 10% glycerol) and put on ice until use. Plasmid DNA (1 μg) was mixed with 40 μl of cells in a chilled Gene Pulser cuvette (0.2 cm). The Gene Pulser apparatus (Bio-Rad Laboratories, Richmond, Calif.) was set at 25 μF and 2.45 kV, and the Pulse Controller at 200 Ω. After electroporation, the *S. thermophilus* cells were immediately resuspended in the rescue broth used for *L. lactis* cells (Hill, C., FEMS Microbiol. Rev. 12: 87–108 (1993)) and incubated for 2 hours at 42° C. before they were plated on GM17 supplemented with the appropriate antibiotic.

Phage isolation

Figure 6:
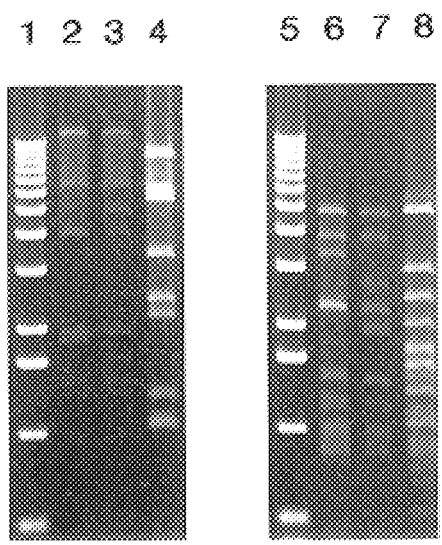
FIG. 6 is an electrophoresis gel showing restriction patterns of ØQ1, ØQ3 and ØQ5. Lane 1 and 5, 1-kb ladder (Bethesda Research Laboratories); Lane 2, ØQ1 DNA cut with EcoRV, Lane 3, ØQ2 cut with EcoRV; Lane 4, ØQ5 cut with EcoRV; Lane 6, ØQ1 cut with MboI; Lane 7, ØQ7 cut with MboI; Lane 8, ØQ5 cut with MboI.

Phages ØQ1 and ØQ3 were recently isolated from yogurt samples whereas ØQ5 and ØQ6 were isolated also in our laboratory but from Mozzarella whey samples. Phages ØQ1 and ØQ3 were then propagated on *S. thermophilus* SMQ-119, ØQ5 on SMQ-173 and ØQ6 on SMQ-174. The genomic DNAs of these streptococcal phages were compared after digestion with EcoRV and MboI (FIG. 6). All four *S. thermophilus* phages had different restriction patterns (FIG. 6) and consequently they were different.

Expression of LlaII in *Streptococcus thermophilus*

Figure 7:
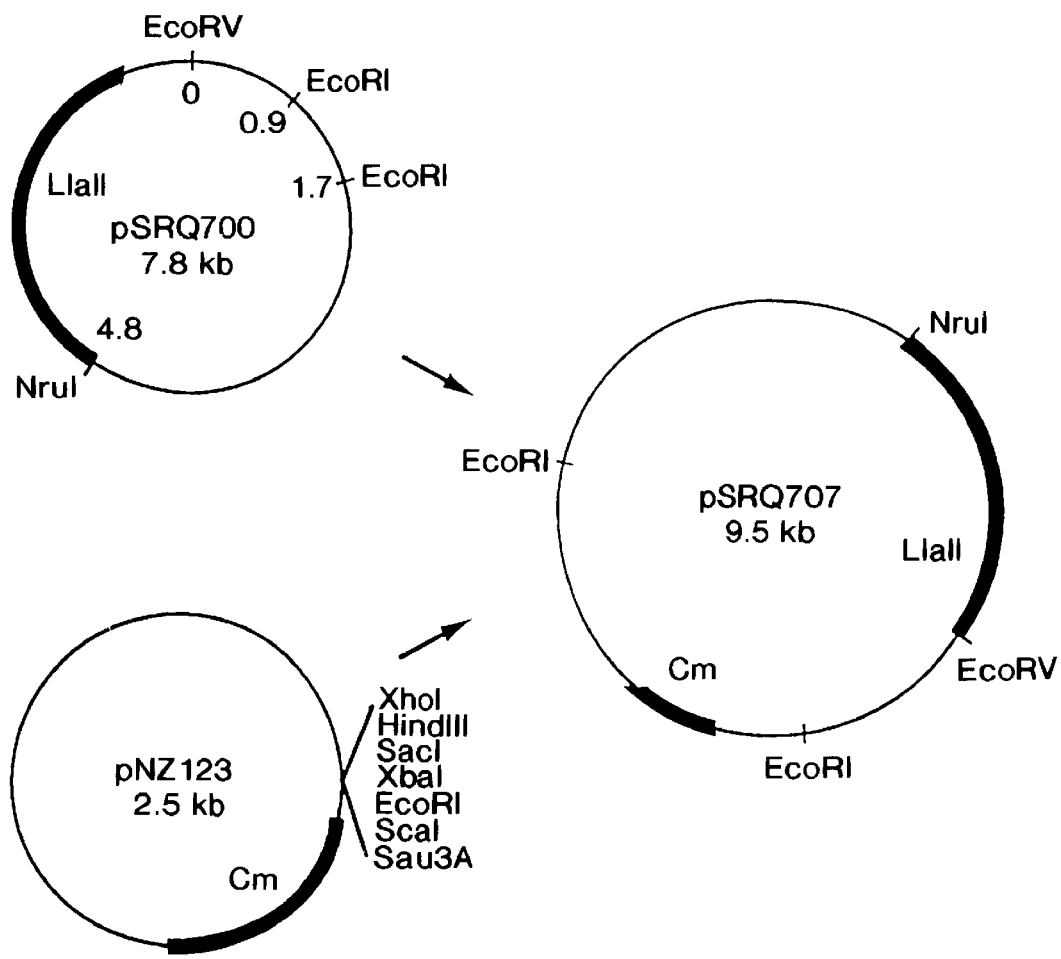
FIG. 7 is a schematic flow sheet showing the construction of the plasmids used in this study.

To verify if LlaII system could be functional in *S. thermophilus*, the LlaII genes were cloned into a vector with an origin of replication functional in *L. lactis* and *S. thermophilus*. The lactic acid bacteria shuttle vector pNZ123 (2.5 kb) (DeVos, W. M., FEMS Microbiol. Rev. 46: 281–295 (1987)) was selected. A 7.0-kb EcoRI fragment from pSRQ700 was cloned into the unique EcoRI site of pNZ123 (FIG. 7). The ligation mixture was electroporated directly into the phage sensitive strain *L. lactis* LM0230. Cm-resistant transformants were obtained and tested for resistance to Øp2. A phage-resistant transformant thus obtained was named SMQ-151. The resulting pNZ123 clone containing the 7.0 kb fragment from pSRQ700 was named pSRQ707. This plasmid was electroporated into *S. thermophilus* SMQ-119 and a Cmr-transformant was named SMQ-154. This clone was tested for resistance against two *S. thermophilus* phages (ØQ1 and ØQ3). Both phages were severely restricted on SMQ-154 since they had EOPs of $10^{-8}$ (Table 5).

TABLE 5

Efficiency of Plaquing of *S. thermophilus* phages on various hosts.

| Phage/Host | EOP |
|---|---|
| ØQ1/SMQ-119 | 1.0 |
| ØQ1/SMQ-146 | 1.0 |
| ØQ1/SMQ-151 | $2.4 \times 10^{-8}$ |
| ØQ3/SMQ-119 | 1.0 |
| ØQ3/SMQ-151 | $6.1 \times 10^{-8}$ |
| ØQ5/SMQ-173 | 1.0 |
| ØQ5/SMQ-211 | $3.9 \times 10^{-6}$ |
| ØQ6/SMQ-174 | 1.0 |
| ØQ6/SMQ-212 | $1.2 \times 10^{-5}$ |

Plasmid pSRQ707 was also electroporated into *S. thermophilus* SMQ-173 and SMQ-174 which are commercially used for Mozzarella cheese production. Transformants were obtained for both strains, and named SMQ-211 and SMQ-212, respectively. Both transformants were tested for phage resistance. Phage Q5 had an EOP of $10^{-6}$ on SMQ-211 whereas ØQ6 and an EOP of $10^{-5}$ on SMQ-212 (Table 5). The phage resistance observed against Mozzarella phages was slightly weaker than with the yogurt phages, but still significant. These results show that the LlaII R/M system is functional in various *S. thermophilus* strains and can confer strong phage resistance in this lactic acid bacteria. This is the first report of increased phage resistance in *S. thermophilus*.

Thus, in general the present invention relates to an isolated and purified *Streptococcus thermophilus* naturally lacking in at least one phage resistance and containing recombinant DNA encoding an endonuclease from a *Lactococcus lactis* to impart the phage resistance.

Further, it relates to a method for fermenting a dairy product, the improvement which comprises using a dairy culture of *Streptococcus thermophilus* lacking in at least one phage resistance for the fermentation incorporating recombinant DNA encoding an endonuclease of *Lactococcus lactis* to impart the phage resistance.

Still further, it relates to a method of imparting phage resistance to a *Streptococcus thermophilus* which is lacking in at least one phage resistance which comprises incorporating recombinant DNA encoding an endonuclease of *Lactococcus lactis* into the *Streptococcus thermophilus* to impart the phage resistance.

The foregoing description is only illustrative of the present invention and the present invention is limited only by the hereinafter appended claims.

---

We claim:

1. An isolated DNA encoding only an enzyme which is selected from the group consisting of LlaIIA, LlaIIB and LlaIIC wherein the DNA is in a sequence which encodes one or more of the enzymes and wherein the enzymes restrict or modify a phage DNA.

2. An isolated DNA having a nucleotide sequence as set forth in SEQ ID NO. 1 and selected from the group consisting of ORF1 (positions 97 to 948), ORF2 (positions 941 to 1747) and ORF3 (positions 1740 to 2651) and combinations thereof.

3. An isolated DNA encoding an enzyme LlaIIA and having a nucleotide sequence as set forth in SEQ ID NO. 1.

4. An isolated DNA encoding an enzyme LlaIIB and having a nucleotide sequence as set forth in SEQ ID NO.1.

5. An isolated DNA sequence encoding an enzyme LlaIIC and having a nucleotide as set forth in SEQ ID NO.1.

6. A recombinant plasmid containing DNA encoding an enzyme which is selected from the group consisting of LlaIIA, LlaIIB and LlaIIC wherein the DNA is in a sequence which encodes one or more of the enzymes and wherein the enzymes restrict or modify a phage DNA.

7. The plasmid of claim 6 which is a shuttle vector PSA3 containing the DNA.

8. A bacterium harboring a recombinant plasmid containing DNA encoding for an enzyme which is selected from the group consisting of LlaIIA, LlaIIB and LlaIIC wherein the DNA is in a sequence which encodes one or more of the enzymes and wherein the enzymes restrict or modify a phage DNA.

9. The bacterium of claim 8 which is *Escherichia coli*.

10. The bacterium of claim 8 which is selected from the group consisting of a *Lactococcus lactis* and *Streptococcus thermophilus*.

11. A method of imparting phage resistance to a bacterium which is sensitive to the phage which comprises incorporating recombinant DNA into the bacterium encoding an enzyme selected from the group consisting of LlaIIA, LlaIIB and LlaIIC wherein the DNA is in a sequence which encodes one or more of the enzymes and wherein the enzymes impart the phage resistance, wherein the DNA is contained in strain *Lactococcus lactis* SMQ-17 deposited as NRRL-B-21337.

12. The method of claim 11 wherein the DNA is in a plasmid.

13. The method of claim 11 wherein the DNA is in a vector for transforming the bacterium.

14. The method of claim 11 wherein the bacterium is selected from the group consisting of a *Lactococcus lactis* and a *Streptococcus salivarius* subsp. *thermophilus*.

15. A bacterium selected from the group consisting of *Streptococcus salivarius* subsp. *thermophilus* and *Lactococ-*

*cus lactis* which group naturally lacks phage resistance which bacterium contains recombinant DNA encoding an enzyme selected from the group consisting of LlaIIA, LlaIIB and LlaIIC wherein the DNA is in a sequence which encodes one or more of the enzymes and has a sequence as set forth in SEQ ID NO: 1 and wherein the enzyme imparts phage resistance.

16. The *Lactococcus lactis* of claim 15 wherein the DNA is contained in *Lactococcus lactis* SMQ-17 deposited as NRRL-B-21337.

17. The *Lactococcus lactis* of claim 15 wherein the DNA is in a plasmid.

18. The *Lactococcus lactis* of claim 15 wherein the DNA is in a vector for transformation.

19. A *Streptococcus thermophilus* naturally lacking in a phage resistance mechanism and containing recombinant DNA encoding at least one endonuclease from *Lactococcus lactis* SMO-17 deposited as NRRL-B-21337 to impart the phage resistance.

20. The *Streptococcus thermophilus* of claim 19 wherein the DNA is in a plasmid.

21. The *Streptococcus thermophilus* of claim 19 wherein the DNA is in a vector for transformation.

22. A method of imparting phage resistance to a *Streptococcus thermophilus* which lacks phage resistance which comprises incorporating recombinant DNA encoding at least one endonuclease of *Lactococcus lactis* SMO-17 deposited as NRRL-B-21337 into the *Streptococcus thermophilus* to impart the phage resistance.

23. The method of claim 22 wherein the DNA is in a plasmid.

24. The method of claim 22 wherein the DNA is in a vector for transforming the bacterium.

* * * * *

UNITED STATES PATENT AND TRADEMARK OFFICE
CERTIFICATE OF CORRECTION

PATENT NO. : 5,824,523
DATED : October 20, 1998
INVENTOR(S) : Sylvain Moineau, Shirley A. Walker, Ebenezer R. Vedamuthu and Peter A. Vandenbergh It is certified that error appears in the above-identified patent and that said Letters Patent is hereby corrected as shown below:

On the title page, "In the Abstract", line 2, "twp" should be --two--.

Column 3, line 56,  N is any of the nucleotide to read  -- N is any of the nucleotides --

Column 10, line 44 (Table 3, column 1), "ØC2*" should be --ØC2--.

Column 12, line 59, "a:F-G-G" should be --α:F-G-G--.

Column 12, line 60, "(FIG. 5)" should be --(FIG. 5A to FIG. 5C)--.

Column 14, line 22, "(FIG. 5)" should be --(FIG. 5A to FIG. 5C)--.

UNITED STATES PATENT AND TRADEMARK OFFICE
CERTIFICATE OF CORRECTION

PATENT NO. : 5,824,523
DATED : October 20, 1998
INVENTOR(S) : Sylvain Moineau, Shirley A. Walker, Ebenezer R. Vedamuthu and Peter A. Vandenbergh It is certified that error appears in the above-identified patent and that said Letters Patent is hereby corrected as shown below:

Column 16, line 27, "Cmr-transformant" should be --$Cm^r$-transformant--.

Column 16, line 53, "Phage Q5", should be --Phage $\varnothing$Q5--.

Column 42, line 1 (Claim 19), "SMO-17" should be --SMQ-17--.

Column 42, line 9 (Claim 22), "SMO-17" should be --SMQ-17--.

Signed and Sealed this

Twenty-ninth Day of June, 1999

Attest:

Q. TODD DICKINSON

*Attesting Officer*   *Acting Commissioner of Patents and Trademarks*